(12) United States Patent
Woehler

(10) Patent No.: US 12,379,204 B2
(45) Date of Patent: *Aug. 5, 2025

(54) SYSTEMS AND METHODS FOR IDENTIFYING LIGHT EMITTING DROPLETS USING AN IMAGE SENSOR AND LENS SYSTEM

(71) Applicant: Christian Woehler, Heidelberg (DE)

(72) Inventor: Christian Woehler, Heidelberg (DE)

( * ) Notice: Subject to any disclaimer, the term of this patent is extended or adjusted under 35 U.S.C. 154(b) by 1371 days.

This patent is subject to a terminal disclaimer.

(21) Appl. No.: 16/948,162

(22) Filed: Sep. 4, 2020

(65) Prior Publication Data

US 2020/0401785 A1    Dec. 24, 2020

Related U.S. Application Data

(63) Continuation of application No. PCT/EP2019/055592, filed on Mar. 6, 2019.

(60) Provisional application No. 62/805,251, filed on Feb. 13, 2019, provisional application No. 62/639,929, filed on Mar. 7, 2018.

(51) Int. Cl.
| | |
|---|---|
| *G01B 11/14* | (2006.01) |
| *G01B 11/00* | (2006.01) |
| *G01B 11/02* | (2006.01) |
| *G01B 11/22* | (2006.01) |
| *G01N 15/1433* | (2024.01) |
| *G01N 21/64* | (2006.01) |
| *G02B 9/06* | (2006.01) |
| *G02B 13/22* | (2006.01) |
| *G02B 21/00* | (2006.01) |
| *G02B 21/36* | (2006.01) |
| *G06T 7/50* | (2017.01) |
| *G06T 7/70* | (2017.01) |
| *G06V 20/69* | (2022.01) |
| *G16B 25/00* | (2019.01) |
| G01N 15/1434 | (2024.01) |
| G02B 21/06 | (2006.01) |
| H04N 23/55 | (2023.01) |

(52) U.S. Cl.
CPC ........... *G01B 11/14* (2013.01); *G01B 11/002* (2013.01); *G01B 11/026* (2013.01); *G01B 11/22* (2013.01); *G01N 15/1433* (2024.01); *G01N 21/6428* (2013.01); *G01N 21/6456* (2013.01); *G02B 9/06* (2013.01); *G02B 13/22* (2013.01); *G02B 21/0008* (2013.01); *G02B 21/361* (2013.01); *G06T 7/50* (2017.01); *G06T 7/70* (2017.01); *G06V 20/693* (2022.01); *G16B 25/00* (2019.02); G01N 2015/1445 (2013.01); G01N 2021/6439 (2013.01); G02B 21/06 (2013.01); H04N 23/55 (2023.01)

(58) Field of Classification Search
CPC ..... G01B 11/14; G01B 11/002; G01B 11/026; G01B 11/22; G06T 7/70; G16B 25/00; G06V 20/693; G01N 15/1433; G01N 21/6428; G01N 21/6456; G02B 9/06; G02B 13/22; G02B 21/0008; G02B 21/361

See application file for complete search history.

(56) References Cited

U.S. PATENT DOCUMENTS

| | | | |
|---|---|---|---|
| 5,784,162 | A | 7/1998 | Cabib et al. |
| 6,072,175 | A | 6/2000 | Wang |
| 6,198,577 | B1 | 3/2001 | Kedar et al. |
| 7,113,617 | B2 | 9/2006 | Kimmel et al. |
| 8,031,918 | B2 | 10/2011 | Roth |
| 8,559,021 | B2 | 10/2013 | Keller-Findeisen et al. |
| 9,041,790 | B2 | 5/2015 | Fine et al. |
| 9,343,494 | B2 | 5/2016 | Lee et al. |
| 9,574,989 | B2 | 2/2017 | Lei |
| 9,715,099 | B2 | 7/2017 | Ozcan et al. |
| 9,743,020 | B2 | 8/2017 | Zheng et al. |
| 9,921,161 | B1 | 3/2018 | Feldkhun |
| 10,838,192 | B2 | 11/2020 | Ozcan et al. |
| 10,871,745 | B2 | 12/2020 | Ozcan et al. |
| 11,353,320 | B2 | 6/2022 | Woehler |
| 2004/0264637 | A1 | 12/2004 | Wang |
| 2012/0032193 | A1 | 2/2012 | Kurokawa et al. |
| 2012/0218379 | A1 | 8/2012 | Ozcan et al. |
| 2016/0041094 | A1 | 2/2016 | Lei |
| 2018/0059222 | A1 | 3/2018 | Pacala et al. |

(Continued)

FOREIGN PATENT DOCUMENTS

| | | |
|---|---|---|
| DE | 102007042984 A1 | 3/2009 |
| KR | 20060080353 A | 7/2006 |
| WO | 9726752 A2 | 7/1997 |

OTHER PUBLICATIONS

International Search Report for International Application No. PCT/EP2019/055592, mailed Sep. 3, 2019, 5 pages.

(Continued)

*Primary Examiner* — Jerry Lin

(74) *Attorney, Agent, or Firm* — Brake Hughes Bellermann LLP

(57) ABSTRACT

An apparatus for identifying a plurality of light emitting droplets includes a detector system having an image sensor comprising an array of pixels and a structure a structure associated with a surface of the image sensor that extends a height away from the surface of the image sensor and defines a field of view for pixels within the array of pixels. The apparatus can additionally include a lens system positioned in front of the image sensor that defines an object space and an image space for the image sensor such that light from a light emitting droplet located in the object space is recorded by a plurality of pixels within the array of pixels.

21 Claims, 9 Drawing Sheets

(56) References Cited

U.S. PATENT DOCUMENTS

2020/0400425 A1  12/2020  Woehler
2020/0401785 A1  12/2020  Woehler

OTHER PUBLICATIONS

Written Opinion for for International Application No. PCT/EP2019/055592, mailed Sep. 3, 2019, 12 pages.
International Search Report for International Application No. PCT/EP2019/055585, mailed Oct. 11, 2019, 5 pages.
Written Opinion for International Application No. PCT/EP2019/055585, mailed Oct. 11, 2019, 12 pages.
Asif, M. Salman, et al., "FlatCam: Thin, Bare-Sensor Cameras using Coded Aperture and Computation", Aug. 31, 2015, retrieved from: http://arxiv.org/pdf/1509.00116v2.pdf on Feb. 17, 2016, XP055250990.
"Canon EOS System", downloaded from https://archive.org/details/EOSSystem0174W970/mode/2up, Jan. 11, 2014, 47 pages.

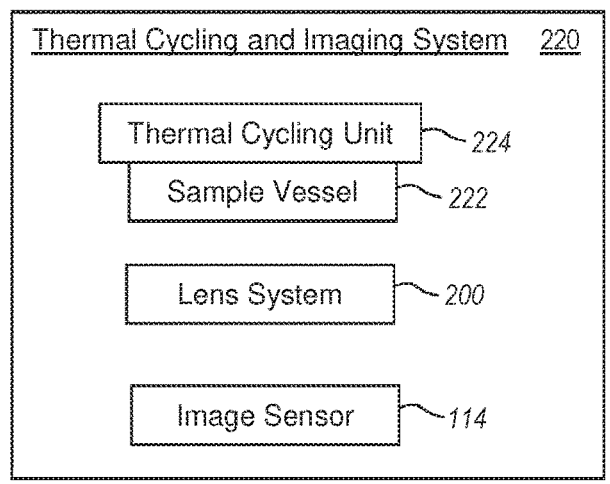
FIG. 13
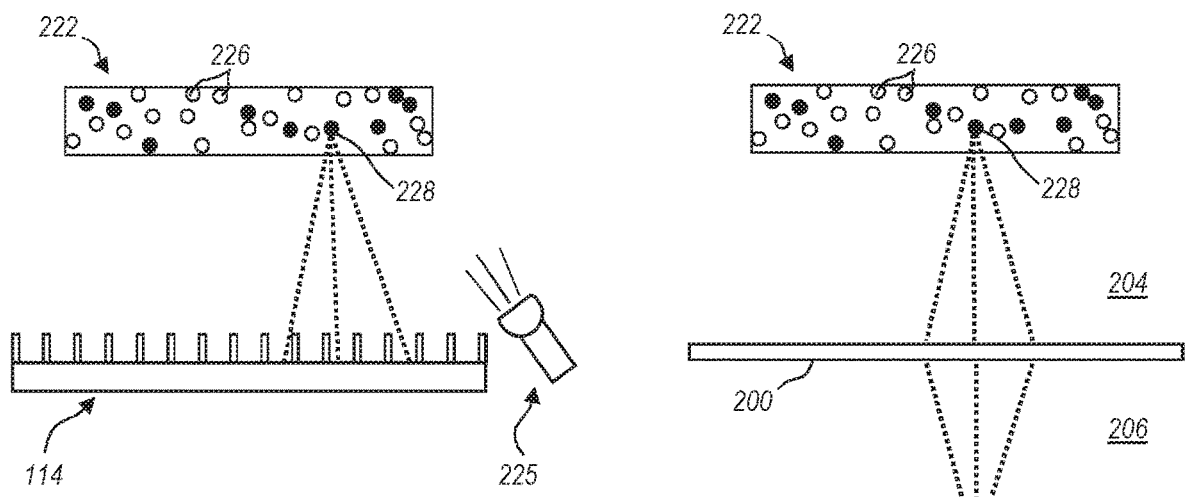
FIG. 14
FIG. 15

SYSTEMS AND METHODS FOR IDENTIFYING LIGHT EMITTING DROPLETS USING AN IMAGE SENSOR AND LENS SYSTEM

CROSS-REFERENCE TO RELATED APPLICATION

This application claims priority to, and is a continuation of, PCT Application No. PCT/EP2019/055592, filed on Mar. 6, 2019, and entitled "SYSTEMS AND METHODS FOR IDENTIFYING LIGHT EMITTING DROPLETS USING AN IMAGE SENSOR AND LENS SYSTEM", which claims the benefit of and priority to U.S. Provisional Application No. 62/639,929, filed on Mar. 7, 2018, and entitled "LENSLESS MICROSCOPY APPARATUSES, SYSTEMS AND METHODS", and U.S. Provisional Application No. 62/805,247, filed on Feb. 13, 2019, and entitled "SYSTEMS AND METHODS FOR IDENTIFYING LIGHT EMITTING DROPLETS USING AN IMAGE SENSOR AND LENS SYSTEM", which are incorporated by reference herein in their entirety.

BACKGROUND

Technical Field

The present application relates to apparatuses, systems, and methods incorporating image sensors. More particularly, the present application relates to apparatuses, systems and methods for identifying one or more microscopic light emitters within an object space using an image sensor and/or real images thereof within an image space defined by an associated lens system.

INTRODUCTION

Microscopy is concerned with observing small, often microscopic, objects. Traditional microscopes incorporate a system of lenses to magnify, and thereby allow viewing of, small objects. In an optical microscope, the system of lenses directs a magnified image of the small object to an eyepiece of the microscope while in a digital microscope, the image is focused on an image sensor. The image sensor records or relays the received image information for display at a monitor. Such traditional lens-based microscopes are frequently large and expensive, and owing to the precision required to view microscopic objects, particularly with high resolution, the optics within most lens-based microscopes are delicate. Traditional lens-based microscopes also have a limited depth of field in which objects are focused in an acceptably sharp manner onto, for example, an image sensor. As a consequence, objects that are located at different distances from the lens have to be placed inside the depth of field of the microscope before they can be investigated with the microscope.

More recently, optofluidic microscopes have been investigated that place a specimen directly on an image chip with or without an additional grid of apertures to obtain images from the chip—and do so without a lens system. These systems appear to use projection imaging with collimated illumination light so that they may not be useable imaging, for example, fluorescent objects. Also, the chips used in these applications have a large pixel pitch, resulting in low resolution. If a grid of apertures is used with the chips in an effort to increase resolution, it disadvantageously requires movement of the specimen during image acquisition.

Also, more recently, artificial apposition compound eyes have been investigated that, imitating insect compound eyes, use an image chip with a pinhole array on the pixels and a further microlens array that focuses light from certain directions on the pinholes. The resolution of the artificial compound eyes is quite low because the construction with pinholes and microlenses has a large pitch, and accordingly, a large pitch CMOS sensor is used.

Known microscopic imaging systems are inefficient for concurrent or sequential imaging of light-emitting droplets within a sample vessel when the volume of the sample is larger than the space that can be monitored with the known systems. This is particularly so for measuring and/or monitoring fluorescent droplets within a sample vessel that are generated by digital PCR or similar methodologies.

Accordingly, there are a number of problems and disadvantages in the field of microscopic imaging that can be addressed.

BRIEF SUMMARY

Various embodiments disclosed herein are related to apparatuses, methods, and systems for identifying the number and/or position of a plurality of light emitting droplets located in object space. Such embodiments beneficially improve microscopy systems, particularly microscopy systems for use identifying light emitting droplets generated by, for example, droplet PCR.

A first aspect provides for an apparatus for identifying a plurality of light emitting droplets includes a detector system having an image sensor comprising an array of pixels and a structure a structure associated with a surface of the image sensor that extends a height away from the surface of the image sensor and defines a field of view for pixels within the array of pixels. The apparatus can additionally include a lens system positioned in front of the image sensor that defines an object space and an image space for the image sensor such that light from a light emitting droplet located in the object space is in the field of view of a plurality of pixels within the array of pixels.

In one embodiment, the light emitting droplet is one of a plurality of light emitting droplets housed within a sample vessel that is disposed within the object space. One or more of the plurality of light emitting droplets can include a nucleic acid and/or a fluorescent marker configured to indicate presence of the nucleic acid.

In one embodiment, the plurality of light emitting droplets additionally include PCR reagents. The light emitting droplets can additionally include a droplet identifying fluorescent marker so that the apparatus can identify each droplet.

In one embodiment, the lens system is configured to project a real image of the plurality of light emitting droplets in the image space of the lens system with the image space being positioned in front of the image sensor. The image sensor and the lens system can be configured such that each of the plurality of light emitting droplets is identifiable and countable by the detector system.

In one embodiment, the detector system is configured to monitor a presence and/or intensity of fluorescence within the plurality of light emitting droplets.

In one embodiment, the apparatus can additionally include a thermal cycler for cycling the plurality of light emitting droplets while the plurality of light emitting droplets is located in the object space.

In one embodiment, the apparatus can additionally include at least a portion of a microfluidic device positioned such that the object space is disposed within at least a portion of the microfluidic device. The apparatus can additionally include a light source, such as an LED, configured to illuminate the object space and/or a beam splitter that is positioned in the path of illumination light provided by the light source to the object space and in the path of light emitted by the plurality of light emitting droplets and recorded by the detector system.

In one embodiment, the light source can include two or more individual light sources, such as two or more individual LEDs, positioned proximate the detector system and around an optical axis of the lens system that are configured to illuminate the object space from different directions. The light source can provide light of two or more different wavelength ranges for exciting different fluorescent markers.

In one embodiment, a density of the plurality of light emitting droplets is greater than or less than a density of the continuous phase so that the plurality of light emitting droplets tends to aggregate at a predefined space within the object space.

The detector system of the disclosed apparatuses can be an integrated unit. The apparatus can additionally include a plurality of detector systems and a plurality of object spaces such that each object space is monitored by at least one detector system. In embodiments having a plurality of object spaces, the plurality of object spaces can have a pitch of 9 mm or a multiple of 9 mm, and a total number of object spaces can be 96 or a divisor of 96.

In one embodiment, the image space defined between the image sensor and the lens system can include a real image of the sample vessel. The real image of the sample vessel can be located in the field of view of the plurality of pixels such that the image sensor records light from the real image of the sample vessel. The lens system can include one or more standard lenses, one or more biconvex lenses, one or more Fresnel lenses, or a combination thereof to form a convergent lens system or a telecentric lens system (e.g., a telecentric lens system having a magnification of the image space of about 1).

In embodiments where the apparatus includes a telecentric lens system, the telecentric lens system may include two or more convergent lens systems with each adjacent pair of convergent lens systems being spaced apart a distance equal to the sum of the focal lengths of each convergent lens system. Each adjacent pair of convergent lens systems can include a proximate convergent lens system and a distal convergent lens system such that the proximate convergent lens system is positioned between the image sensor and the distal convergent lens system and the focal length of the proximate convergent lens system is less than or equal to the focal length of the distal convergent lens system.

In one embodiment, an axial magnification of the adjacent pair of convergent lens systems increases the object space in a direction perpendicular to the image sensor. For example, the object space can be extended between 0.5 mm and 20 mm in a direction perpendicular to the image sensor. Additionally, or alternatively, the image space can be at least two times smaller (e.g., between two and fifty times smaller, between six and ten times smaller, or more than fifty times smaller) than the object space in a direction perpendicular to the image sensor.

As provided above, the apparatus can include an image sensor having a structure associated therewith. The structure may be associated with a surface of the image sensor and include a plurality of walls positioned on pixel boundaries, forming a regular grid (e.g., around each pixel or around a set of pixels, comprising groups of neighboring pixels). In one embodiment, the plurality of walls additionally includes a horizontal structure disposed on top of the walls such that a cross-section of a wall within the plurality of walls forms a T-profile.

The image sensor can have a pixel pitch between about 0.8 μm-10 μm, such as about 1 μm, and the height of the structure associated with the image sensor can be between about 0.4 μm-30 μm or between 0.5 and 3 times the pixel pitch of the image sensor. The image sensor can additionally include comprises a backside illuminated chip for increasing a light sensitive area of each pixel or each set of pixels within the array of pixels.

In one embodiment, the apparatus further includes one or more optical filters associated with the structure to limit light recorded at the array of pixels to one or more wavelength ranges. The one or more optical filters can be arranged in a color filter array, for example, so that adjacent pixels record light of different wavelength ranges. In one aspect, the structure includes or is made at least partially of a low-reflective or non-reflective material, such as a metal and/or other material with a high absorption coefficient.

Embodiments of the present disclosure additionally include systems for monitoring fluorescence in a sample vessel. Such systems can include a plurality of apparatuses, as summarized above and described in greater detail below in addition to a multi-well plate. The sample vessel associated with each apparatus of the plurality of apparatuses can include a well within the multi-well plate.

In one embodiment, the system is a system for monitoring droplet polymerase chain reaction (PCR). Such a system may include a sample vessel having a plurality of droplets such that each droplet of the plurality of droplets includes PCR reagents and a subset of the plurality of droplets includes nucleic acid. The system can additionally include a thermal cycler operably connected with the sample vessel and a detector system made up of at least an image sensor, a structure associated with the image sensor and defining a field of view for the image sensor, and a lens system positioned within the field of view and defining an image space for the image sensor. The detector system can be positioned such that the sample vessel is within the image space and a real image of the plurality of droplets is imagable by the image sensor.

In one embodiment, the system for monitoring droplet PCR includes an image processor configured to identify and/or count a number of light-emitting droplets within the plurality of droplets. Counting the light-emitting droplets can include capturing a light intensity value at each photo-activated pixel of the image sensor and identifying local maxima of light intensity based on the light intensity values. Alternatively, counting the number of light-emitting droplets can include capturing a light intensity value at each photo-activated pixel of the image sensor, identifying a first light-emitting droplet having a local maximum of light intensity and a corresponding light profile associated with the local maximum, subtracting the local maximum and the corresponding light profile from the captured light intensity values, and identifying subsequent light-emitting droplets for each remaining local maximum and corresponding light profile. Additionally, or alternatively, the image processor can be configured to identify a relative concentration of nucleic acid between each light-emitting droplet within the subset of droplets.

In one embodiment, the system includes a color filter array for detecting at least two different wavelengths of light.

In one embodiment, each droplet of the plurality of droplets includes at least a first and second fluorophore. The first fluorophore can be configured to identify each of the plurality of droplets and the second fluorophore can be configured to identify the subset of droplets comprising nucleic acid. Alternatively, the first fluorophore can identify a first multiplex PCR amplification product and the second fluorophore can identify a second multiplex PCR amplification product.

Embodiments of the present disclosure additionally include methods for identifying light-emitting droplets. In one embodiment, a method for identifying light-emitting droplets includes at least the step of thermal cycling a sample vessel having a plurality of droplets. The droplets can include PCR reagents and a nucleic-acid-binding fluorophore, and at least a subset of the plurality of droplets can include nucleic acid. The method can additionally include monitoring the sample vessel using a detector system that includes an image sensor, a structure associated with the image sensor and defining a field of view for the image sensor, and a lens system positioned within the field of view and defining an image space for the image sensor such that the sample vessel is positioned within the image space of the detector system. The method can additionally include capturing a light intensity value at each photoactivated pixel of the image sensor receiving light from a real image of the sample vessel disposed in the image space and identifying a number of light-emitting droplets based on the light intensity values.

In one embodiment, the step of identifying a number of light-emitting droplets includes counting a number of local maxima of light intensity. Alternatively, identifying a number of light-emitting droplets can include (i) determining a local maximum of light intensity and a corresponding light profile associated with the local maximum, (ii) subtracting the local maximum and the corresponding light profile from the captured light intensity values, and (iii) repeating steps (i) and (ii) for each subsequent local maximum and corresponding light profile.

Embodiments of the present disclosure additionally include methods for identifying a light emitting droplet disposed in object space. In one embodiment, a method for identifying a light emitting droplet disposed in object space includes (i) providing an image sensor including an array of pixels arranged in rows and columns and a structure associated with and extending a height away from a surface of the image sensor, the structure defining a field of view for each pixel within the array of pixels, (ii) determining a light intensity value for each of a plurality of photoactivated pixels, the plurality of photoactivated pixels receiving light from the light emitting droplet disposed in the object space, and (iii) identifying a first photoactivated pixel having a local maximum of light intensity, the first photoactivated pixel being closer to the light emitting droplet than other pixels of the plurality of photoactivated pixels receiving less light than the first photoactivated pixel.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 13 illustrates a general schematic of a thermal cycling and imaging system for identifying a plurality of light emitting droplets;

FIG. 14 illustrates an exemplary embodiment of a sample vessel having a plurality of light emitting droplets identified by a detector system;

FIG. 15 illustrates an exemplary embodiment of a sample vessel having a plurality of light-emitting droplets where a real image of the light-emitting droplets is identified by the associated image sensor of the displayed detector system;

DETAILED DESCRIPTION

Figure 1:
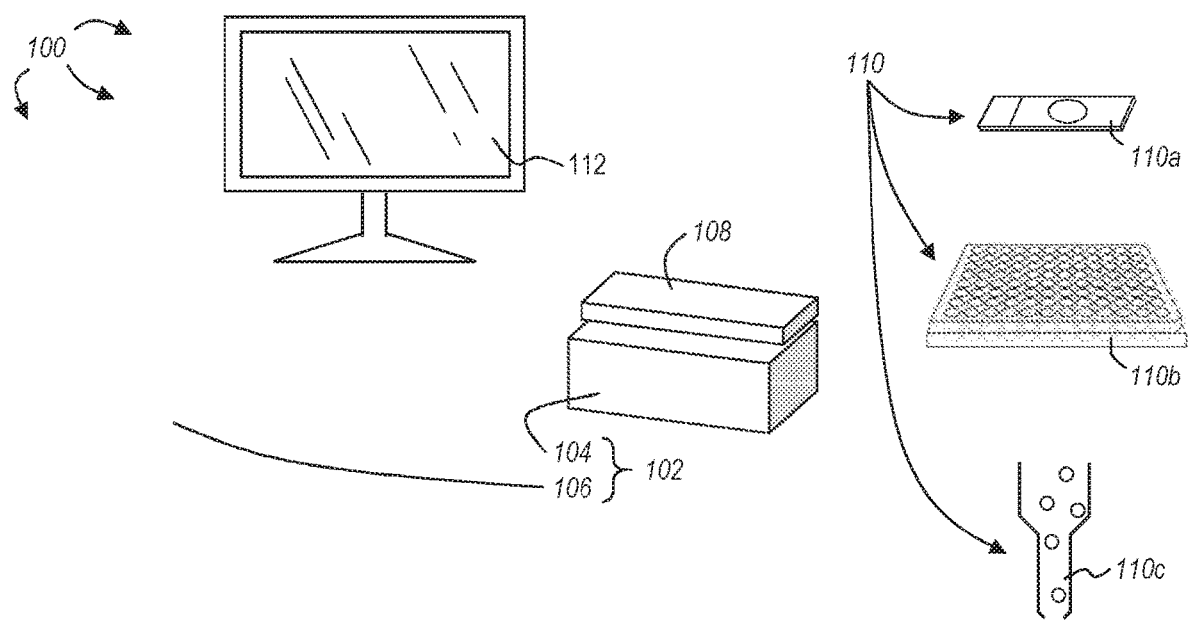
FIG. 1 illustrates an example embodiment of a system incorporating features disclosed or envisioned herein.

As used in the specification, a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. In addition, unless otherwise indicated, numbers expressing quantities, constituents, distances, or other measurements used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Furthermore, as used in the specification and appended claims, directional terms, such as "top," "bottom," "left," "right," "up," "down," "upper," "lower," "proximal," "adjacent," "distal," and the like are used herein solely to indicate relative directions and are not otherwise intended to limit the scope of the specification or claims.

Overview of Imaging Systems and Methods

Embodiments disclosed or envisioned herein may comprise or utilize a special purpose or general-purpose computer including computer hardware, such as, for example, one or more processors, as discussed in greater detail below. Embodiments may also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments can comprise at least two distinctly different kinds of computer-readable media: computer storage media and transmission media.

Computer storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired and wireless) to a computer, the computer properly views the connection as a transmission medium. Transmission media can include a network and/or data links which can be used to carry data or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., an "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that embodiments may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, tablets, smart phones, routers, switches, and the like. Embodiments may be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. Program modules for one entity can be located and/or run in another entities data center or "in the cloud." In this specification and in the following claims, a computer system is also defined to include imaging systems (e.g., imaging system 102 in FIG. 1).

FIG. 1 illustrates an exemplary system 100 incorporating features disclosed or envisioned herein. At the heart of the system 100 is an imaging system 102 in which samples, such as biological cells, are imaged and analyzed. The exemplary imaging system 102 includes, but is not limited to, an image sensor assembly 104 and a computing device 106. Within the image sensor assembly 104 is an image sensor (e.g., image sensor 114 of FIG. 2) configured to capture image data from a sample positioned within the field of view of the image sensor. In a general working example, a sample 110 is placed directly on the image sensor assembly 104 or otherwise positioned within the field of view of the image sensor within assembly 104. The image sensor captures image data from the sample 110, which is further analyzed, as described below, to create a three-dimensional (3D) image of the object space containing the sample and components disposed therein. In a preferred embodiment, the image sensor assembly 104 captures image data from one or more light emitters within the sample, and based on the image data, constructs a 3D image of the observed object space, including the positions of light emitters within the object space with sub-pixel resolution. In the following, the term light emitter may be used interchangeably with the term light emitting droplet.

According to embodiments, light emitters or light emitting droplets may emit light because they include molecules or substances that emit light. Light emission may be based on luminescence such as, for example, chemiluminescence or fluorescence. Light emitters may include, for example, fluorophores or quantum dots. Light emitters may include target molecules (e.g., DNA, RNA, proteins, inorganic molecules) or target objects (e.g., cells, beads, larger structures or certain parts of larger structures) and they may include light emitting molecules or substances associated with the target molecules or target objects to identify the target molecules or target objects and/or to count them or to reconstruct the position of the light emitters (i.e. light emitting droplets) in three-dimensional space.

Embodiments of the present disclosure can identify light emitters using a single image of a volume of space that is large in comparison with a volume that, for example, a traditional light microscope can sharply focus onto an image sensor. In an example, different types of light emitters may be used to identify different targets. The light emitters may emit light at different characteristic wavelengths, and embodiments of the present disclosure may be able to identify the different light emitters by their characteristic wavelengths. This may be achieved, for example, in embodiments using a color filter array above the pixels of the image sensor. As an additional example, embodiments of the present disclosure may also take multiple images in given time period (e.g., 24 or 30 images per second) to record any movement of the light emitters and/or any change in light emission intensity.

As shown in FIG. 1, a stage housing 108 can be mounted on or otherwise be associated with the image sensor assembly 104 to facilitate illumination and/or positioning of the sample 110. The sample can be included within or mounted on any sample receiving apparatus, including, for example, a microscope slide 110a, a multi-well plate (e.g., a 96-well plate 110b shown in FIG. 1), a flow cell 110c, or similar. Accordingly, the stage housing 108 can include one or more light sources to illuminate the sample 110, which can be, for example, a white light or a light of a defined wavelength. In embodiments where the light emitter includes a fluorophore, the light source can include a fluorophore excitation light source. For example, the stage housing 108 can include a light engine comprising multiple light emitting diodes (LEDs) configured to emit an excitation wavelength for exciting fluorophores within the sample 110. Additionally, or alternatively, the stage housing 108 can include optical filters that filter the excitation and emission light, such as a multi-position dichroic filter wheel and/or a multi-position emission filter wheel.

As a general method of operation, a fluorophore excitation source can be automatically or manually directed to provide multiple bandwidths of light ranging from violet (e.g., 380 nm) to near infrared (e.g., at least 700 nm) and are designed to excite fluorophores, such as, for example, cyan fluorescent protein (CFP) and Far Red (i.e., near-IR) fluorophores. Example LED bandwidths with appropriate excitation filters (e.g., as selected via a computing device 106 driven excitation filter wheel) can include, but are not limited to, Violet (380-410 nm LED & 386/23 nm excitation filter), Blue (420-455 nm LED & 438/24 nm excitation filter), Cyan (460-490 nm LED & 485/20 nm excitation filter), Green (535-600 nm LED & 549/15 nm excitation filter), Green (535-600 nm LED & 560/25 nm excitation filter), Red (620-750 nm LED & 650/13 nm excitation filter), and Near-IR (700-IR nm LED & 740/13 nm excitation filter). The two Green/excitation filter combinations listed above can be provided optionally via, for example, a mechanical flipper, when desiring to improve the brightness of red and scarlet dyes. Of course, other LED bandwidths can also be used.

Additionally, or alternatively, the stage housing 108 can include a stage assembly and positioning mechanism configured to retain and selectively move sample for viewing by the image sensor, as known in the art. As it should be appreciated, the stage assembly can be configured to move within any of three-dimensions, as known in the art. For example, the stage assembly can be configured to move laterally (e.g., in an x, y-plane parallel to the surface of the image sensor) to position different portions of the sample within the field of view of the image sensor. The stage assembly can additionally, or alternatively, be configured to move in a z-direction (e.g., between parallel x, y-planes that are each disposed at different distances from the surface of the image sensor) using any mechanism known in the art, such as, for example, a stepper motor and screw/nut combination providing step-wise movements of the sample toward/away from the image sensor in increments down to 0.006 μm/microstep.

In some embodiments, it can be advantageous to control or adjust the distance between the sample, or the closest light emitter within the sample, and the image sensor of the assembly 104—or in other words, to adjust the object space viewed by the image sensor within assembly 104. Doing so, it may be possible to adjust the object space such that a desired number of light emitters (or other portion of the sample) is in the field of view of a desired number or percentage of pixels within the array of pixels defining the image sensor. For example, the stage assembly can position the sample such that a desired number of light emitters (or defined portion of the sample) is in the field of view of at least nine pixels and/or of less than 90% of the pixels within the array of pixels defining the image sensor. Doing so can optimize and/or increase the accuracy of the system in determining the three-dimensional position of light emitters within the object space, as detailed more fully below.

Upon capturing image data at the image sensor, the data can be analyzed and/or stored locally at the image sensor assembly 104 and/or in conjunction with the computing device 106. This can include, for example, constructing the position of light emitters within the sample/object space. The computing device 106 can additionally be used as a controller for the system as well as for performing, by itself or in conjunction with image sensor assembly 104, the analysis and/or storage of data obtained by image sensor assembly 104. Computing device 106 can comprise a general purpose or specialized computer or server or the like, as defined above, or any other computerized device. Computing device 106 can communicate with image sensor assembly 104 directly or through a network, as is known in the art. In some embodiments, computing device 106 is incorporated into the image sensor assembly 104. In some embodiments, the computing device is incorporated within the image sensor assembly.

System 100 can also include a user display device 112 to display results and/or system configurations. Image sensor assembly 104 and/or computing device 106 can communicate, either directly or indirectly, with user display device 112 and can cause the position of the light emitter within object space to be displayed on the user display device 112. For example, the computing device 106 can construct a 3D image of the observed object space with each identified light emitter positioned within the 3D image.

In one embodiment, one or more of the method steps described herein are performed as a software application. However, embodiments are not limited to this and method steps can also be performed in firmware, hardware or a combination of firmware, hardware and/or software. Furthermore, the steps of the methods can exist wholly or in part on the image sensor assembly 104, computing device 106, and/or other computing devices.

An operating environment for the devices of the system may comprise or utilize a processing system having one or more microprocessors and system memory. In accordance with the practices of persons skilled in the art of computer programming, embodiments are described below with reference to acts and symbolic representations of operations or instructions that are performed by the processing system, unless indicated otherwise. Such acts and operations or instructions are referred to as being "computer-executed," "CPU-executed," or "processor-executed."

Exemplary Image Sensor Assemblies

Figure 2:
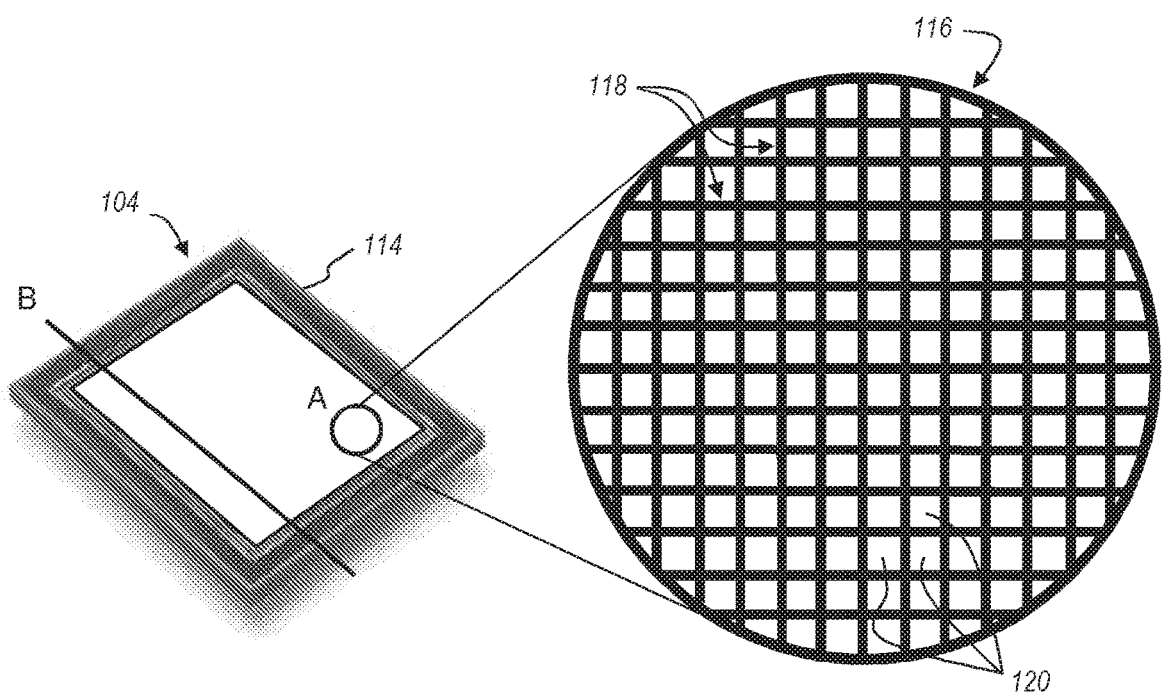
FIG. 2 illustrates a schematic of an image sensor having a structure associated therewith such that the structure surrounds each pixel, forming a regular grid.

As described above, the imaging system 102 can include an image sensor assembly 104. As shown in FIG. 2, the image sensor assembly 104 can include an image sensor 114 and a structure 116 associated with the surface of the image sensor 114. The image sensor 114 can be any CCD or CMOS sensor array or chip having an array of pixels arranged in rows and columns, as shown, for example, in the magnified view (A) of FIG. 2.

In the exemplary embodiment of FIG. 2, the structure 116 includes a plurality of walls 118 positioned on the pixel boundaries, forming a regular grid. Accordingly, each pixel 120 of the array of pixels is bounded by walls 118 of the structure 116. It should be appreciated, however, that while the structure 116 of FIG. 2 illustrates walls 118 positioned on each pixel boundary such that each individual pixel 120 is bounded by walls 118, other arrangements or spacing of the walls can be used. For example, the walls of the structure could bound a set of pixels (e.g., a 2×1, 2×2, 2×3, 3×3, or larger set of pixels). Additionally, or alternatively, the walls could be positioned off of the pixel boundary, within the light receiving area of the pixels. In a preferred embodiment, the walls of the structure are positioned on the pixel boundaries.

To overcome the limitations of prior art image sensors, which fail to maintain high resolution capacity while obtaining image data of stationary objects for determining the position of the objects in object space, the structures disclosed herein extend a height away from the surface of the image sensor and thereby define a field of view for each pixel. This enables an object, such as a light emitter, to be positionally located without requiring the object to move relative to the image sensor. For example, based on the number and location of pixels receiving light from a light emitter for a given image sensor and structure, the z-distance between the surface of the image sensor and the light emitter can be determined along with the x- and y-coordinates with respect to the image sensor. Using these data, the three-dimensional object space comprising the light emitter can be modeled, along with the position of the light emitter within the object space.

Applications of this technology can be used to improve various microscopy systems and methods. For example, a 3D model is traditionally obtained by compiling z-sequences of optical slices of a sample (e.g., using confocal laser scanning microscopy or traditional wide-field microscopy), but this requires imaging each of a plurality of focal planes and compiling or stacking these image sections to form the 3D image stack comprising the model. Accordingly, the position of light emitters, such as fluorescing portions of the sample, within the 3D model are given a contextual position within the sample by comparing images of adjacent focal planes. Instead of capturing a host of images at different focal planes and assembling these images to render a 3D model, the systems of the present disclosure can—with a single image—identify the three-dimensional position of objects within the object space containing at least a portion of the corresponding sample.

Clearly, the systems and methods disclosed herein offer significant advantages over prior art microscopy systems and methods. Because a single image is sufficient to render the three-dimensional positions of objects within a sample, there is no need to move the sample through a series of z-sequences, and therefore, expensive motors required for positioning the sample at each optical slice of the z-sequence are not necessary. This reduces the cost and mechanical and operational complexity of microscopy systems. Images can be obtained more quickly and with a reduced digital storage cost (e.g., because an associated computing system only stores data corresponding to a single image instead of data corresponding to stacks of images and the spatial relationships between each image of the stack).

Additional advantages are seen particularly within applications of fluorescence microscopy. Photobleaching is a well-known problem in fluorescence microscopy; in essence, the longer a fluorophore is exposed to excitation light, the less light it emits until it no longer emits light in response to excitation. This is particularly problematic in instances where a large sample is imaged or where multiple focal planes are imaged. For large samples, fluorophores outside of the viewing area often receive incident excitation radiation, causing photobleaching of responsive fluorophores outside the viewing area, and when these fluorophores are eventually imaged, their fluorescence intensity is reduced from their original state. This can limit the usefulness of the data. For example, such photobleaching can make it difficult to quantify and compare fluorescence intensity of objects between viewing areas of a large image.

Similarly, in situations where a series of images are captured at different focal planes, excitation light is directed at a single viewing area for a prolonged period of time, and images captured later within the z-sequence are likely to suffer from photobleaching—again limiting the usefulness of the data. Additionally, the resolution of optical slices or the resultant 3D model can be limited by photobleaching. That is, resolution can be dependent upon a combination of how quickly the fluorophores photobleach and how quickly each optical slice can be captured. A faster capture rate of optical slices often results in a greater number of low-resolution optical slices. This allows for more precise positioning of objects within the sample but comes at the cost of a lower resolution for each optical slice. On the other hand, a smaller number of high-resolution slices offers greater clarity at each optical slice but comes at the cost of a lower resolution 3D model of the sample and less precise positioning of objects within the sample.

The disclosed systems and methods beneficially reduce the amount of time fluorophores are exposed to excitation light without sacrificing—or in some cases increasing—the precision by which the position of objects, such as light emitters, can be determined within the sample. Further, because the location of fluorescent objects within the sample can be determined quickly and without significant photobleaching, the systems and methods disclosed herein can enable the image sensor to image a desired optical volume quickly and precisely. For example, a single image can be captured and the position of a light emitter determined therefrom independently of where the light emitter is located within the defined object space. In a further example, the whole object space can be monitored by reading out the image sensor multiple times in a given time period (e.g., 24 or 30 times a second). This can enable the disclosed system to record movement of one or more light emitters within the object space and/or changes in the intensity of light emitted by the one or more light emitters within the object space.

Figure 3:
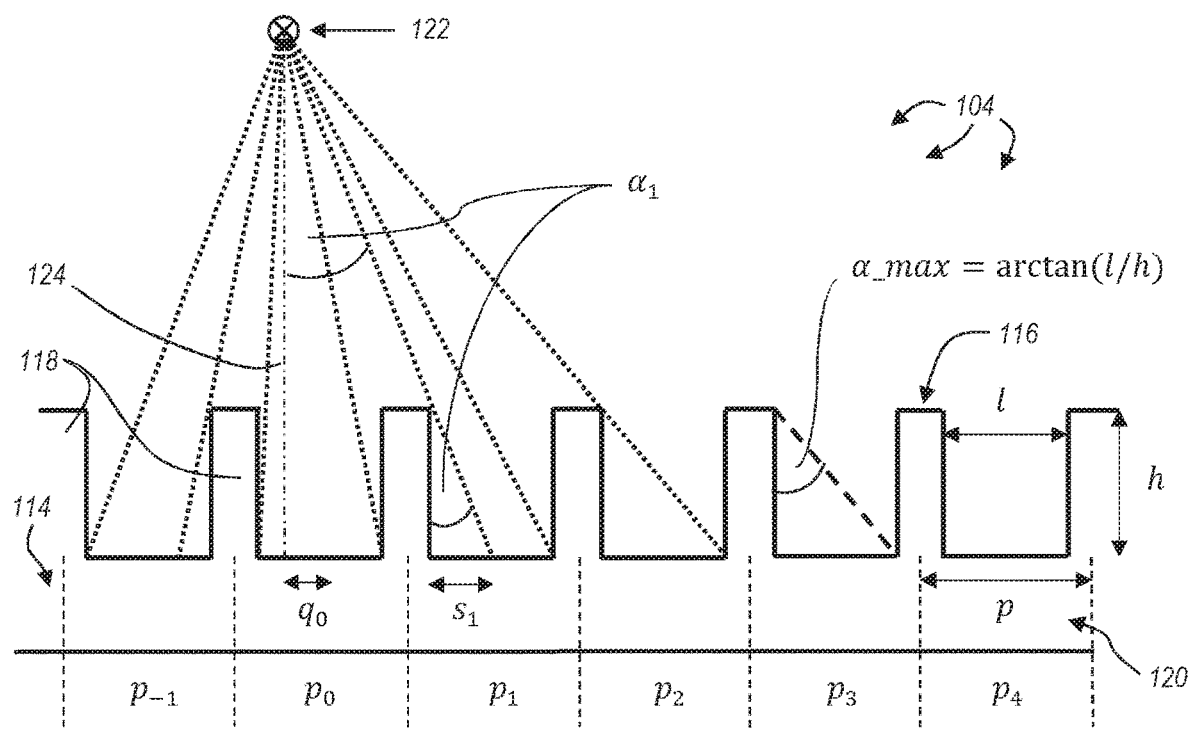
FIG. 3 is a cross-sectional side view of the image sensor and associated structure of FIG. 2, showing a light emitter disposed a height above the image sensor.

With continued reference to FIG. 2, an image sensor 114 having regular rectangular walls 118 around each pixel 120 is shown. In other words, the walls 118 are positioned on the pixel boundaries and form a regular grid. A cross-sectional side view (taken along line (B)) of the image sensor 114 and associated structure 116 is shown in FIG. 3. Referring thereto, it is possible to calculate the area of each pixel 120 that receives light from a light emitter 122 depending on the position of the light emitter 122 with respect to the array of pixels 120 of the image sensor 114. In an approximation, the product of the area of a pixel 120 receiving light and the solid angle of the light receiving area of the pixel 120 with respect to the light emitter 122 is assumed to be proportional to the light intensity measured by the pixel 120. Using the measured values of the pixels and the calculation, it is possible to determine the position of the light emitters 122 in three-dimensional object space and with further input also the brightness of the light emitters 122. In any one of the embodiments, a light emitter may be an object or substance that is capable of providing light. A light emitter may be, e.g. a luminescent substance such as a fluorescent substance or fluorescent molecule or it may be illuminated object. The light provided by a light emitter may include light of the visible wavelength range, the infrared wavelength range, and/or the ultraviolet wavelength range. The light may include the wavelength range that is measurable by image sensors with pixels.

An exemplary calculation is described below with reference to the light emitter 122 and image sensor assembly 104 of FIG. 3.

As shown in the cross-sectional side view of image sensor assembly 104, p is the pixel pitch, l is the side length of the light sensitive area of the pixels 120 (p=l+d with d being the thickness of the walls 118), h is the height of the walls 118, $p_0$ is the pixel 120 which is closest to the light emitter 122 (i.e., the pixel 120 is located at the position through which a line 124 that is perpendicular to the image sensor passes between the image sensor 114 and the light emitter 122), the pixels $p_1$ are the pixels 120 that are i pixels far from $p_0$ in a row (or column) of the image sensor 114. $q_0$ is the distance in the −i direction between the center of pixel $p_0$ and the line 124 that is perpendicular to the image sensor 114 and goes through the light emitter 122 ($q_0$ can be positive or negative). $s_1$ is the length of the shadow that is cast by the wall 118 between pixel $p_0$ and $p_1$. α_max is the maximal angle at which light from the light emitter 122 is received at the pixels 120. $\alpha_1$ is the angle between the wall 118 between pixel $p_0$ and $p_1$ and the light that just reaches the light sensitive area of the pixel $p_1$, and it is also the angle between the line 124 and the light that just reaches the light sensitive area of the pixel $p_1$.

In some embodiments, the walls 118 are made of or include a low-reflective material, preferably a non-reflective material. The material may additionally, or alternatively, have a high absorption coefficient or can be metal which additionally, or alternatively, can absorb the light. Correction factors taking into account, for example, reflections may be used in the following calculations if this is not the case.

One factor of the light intensity that is measured by a pixel $p_i$ is proportional to the area of the light sensitive area of the pixel that receives light from the light emitter 122. As a simplification, it can be assumed that the light sensitive area includes all of the bottom of the wells (i.e., the area between the walls) and that the measurement efficiency of the light sensitive area does not depend on the angle at which the light hits on the image sensor 114 given the restricted range of angles at which light is measured. If these assumptions are not justified, further correction factors may be included in the following calculation.

The distance of the light emitter 122 to the bottom of the wells is taken as r so that the distance of the light emitter 122 to the top of the wells is r−h. The shadow length $s_i$ for pixel $p_i$, i>0, is the following:

$$s_i = h \cdot \tan(\alpha_i)$$

$$\tan(\alpha_i) = (q_0 + l/2 + i \cdot d + (i-1) \cdot l)/(r-h) = \left(q_0 - \frac{l}{2} + i \cdot p\right)/(r-h)$$

From this follows $$s_i = h \cdot (q_0 - l/2 + i \cdot p)/(r-h).$$

For i<0, it is $$s_i = h \cdot \left(-q_0 - \frac{l}{2} - i \cdot p\right)/(r-h)$$

$$= h \cdot (\mathrm{sgn}(i) \cdot q\_0 - l/2 + |i| \cdot p)/(r-h),$$

where sgn(x) is +1 for x≥0 and −1 for x≤0 and abs(x) is +x for x≥0 and −x for x<0.

For i≠0, it is then $$s_i = h \cdot (\mathrm{sgn}(i) \cdot q_0 - l/2 + |i| \cdot p)/(r-h).$$

For i≠0, it is $$s_i = h \cdot (|q_0| - l/2) \cdot \text{step}(|q_0| - l/2)/(r-h),$$

where step(x) is 0 for x<0 and 1 for x≥0. The reason for this is that the light emitter 122 casts only a shadow in the i-direction of the closest pixel if the light emitter 122 is positioned above the wall 118 which is positioned at l/2 from the pixel center.

The area of pixel $p_i$, i>0, that measures light from the light emitter 122 is proportional to $l-s_i$. It follows for the side length $\alpha_1$ of pixel $p_i$ that receives light from the light emitter 122

$$\alpha_i = l - s_i$$
$$= l - h \cdot (\text{sgn}(i) \cdot q_0 - l/2 + |i| \cdot p)/(r-h)$$
$$= (1/(r-h)) \cdot (l - h \cdot (\text{sgn}(i) \cdot q_0 - l/2 + |i| \cdot p)), \text{ for } i \neq 0.$$

This result is only valid for i≠0 and $\tan(\alpha_i) = (\text{sgn}(i) \cdot q_0 + l/2 + |i| \cdot p)/(r-h) < (l/h)(= \tan(\alpha\_\max))$. From the second limitation follows the upper absolute bound for $|i|$: $|i| < (r \cdot l/h - \text{sgn}(i) \cdot q_0 - l/2)/p$.

For i=0, it is $$a_i = l - h \cdot (q_0 - l/2) \cdot \text{step}(q_0 - l/2)/(r-h).$$

The same calculation can be made for the direction perpendicular to the i-direction of the image sensor 114 (i.e., in the direction of the column or row respectively) to give the following result for the area $a_{i,j}$ of the pixels that receives light from the light emitter 122 that has as the closest pixel $p_{i_0,j_0}$:

$$a_{i,j} = \left(\frac{1}{(r-h)^2}\right) \cdot \left[r \cdot l - h \cdot \left(\text{sgn}(i-i_0) \cdot q_{0,i} + \frac{l}{2} + |i-i_0| \cdot p\right)\right] \cdot$$
$$\left[r \cdot l - h \cdot \left(\text{sgn}(j-j_0) \cdot q_{0,j} - \frac{l}{2} + |j-j_0| \cdot p\right)\right] =$$

$$\left[l - h \cdot \frac{\begin{pmatrix} \text{sgn}(i-i_0) \cdot \\ \left(q_{0,i} - \frac{l}{2}\right) + \\ |i-i_0| \cdot p \end{pmatrix}}{r-h}\right] \cdot \left[l - h \cdot \frac{\begin{pmatrix} \text{sgn}(j-j_0) \cdot \\ \left(q_{0,j} - \frac{l}{2}\right) + \\ |j-j_0| \cdot p \end{pmatrix}}{r-h}\right],$$

⟦*⟧ for $|i - i_0| > 0$ and $|j, -j_0| > 0$ and for $$|i - i_0| < \left\lfloor \frac{\left(\frac{rl}{h} - \text{sgn}(i-i_0) \cdot q_{0,i} - \frac{l}{2}\right)}{p} \right\rfloor \text{ and}$$

$$|j - j_0| < \left\lfloor \frac{\left(\frac{rl}{h} - \text{sgn}(j-j_0) \cdot q_{0,j} - \frac{l}{2}\right)}{p} \right\rfloor.$$

For $i = i_0$ and $|i - i_0| > 0$, it is $$a_{i_0,j} = \left[l - h \cdot \frac{\left(|q_{0,i}| - \frac{l}{2}\right) \cdot \text{step}\left(|q_{0,i}| - \frac{l}{2}\right)}{r-h}\right] \cdot \left[l - h \cdot \frac{\begin{pmatrix} \text{sgn}(j-j_0) \cdot \\ \left(q_{0,j} - \frac{l}{2}\right) + \\ |j-j_0| \cdot p \end{pmatrix}}{r-h}\right] \cdot \llbracket * \rrbracket$$

For $j = j_0$ and $|j_0| > 0$, it is $$a_{i,j_0} = \left[l - h \cdot \frac{\begin{pmatrix} \text{sgn}(i-i_0) \cdot \\ q_{0,i} - \frac{l}{2} + \\ |i-i_0| \cdot p \end{pmatrix}}{r-h}\right] \cdot \left[l - h \cdot \frac{\left(|q_{0,j}| - \frac{l}{2}\right) \cdot \text{step}\left(|q_{0,j}| - \frac{l}{2}\right)}{r-h}\right] \cdot \llbracket * \rrbracket$$

For $i = i_0$ and $j = j_0$, it is $$a_{i_0,j_0} = \left[l - h \cdot \frac{\left(|q_{0,i}| - \frac{l}{2}\right) \cdot \text{step}\left(|q_{0,i}| - \frac{l}{2}\right)}{r-h}\right] \cdot \left[l - h \cdot \frac{\left(|q_{0,j}| - \frac{l}{2}\right) \cdot \text{step}\left(|q_{0,j}| - \frac{l}{2}\right)}{r-h}\right] \cdot \llbracket * \rrbracket$$

As a special case, $a_{i_0,j_0} = l^2$ for $|q_{0,i}| < l/2$ and $|q_{0,j}| < l/2$.

Equations ⟦*⟧ describe the light sensitive area that records light from a single light emitter 122 that is point like (has no extension which is a good approximation of a light emitter that is much smaller than, for example, the pixel pitch).

It should be appreciated that FIG. 3 can be viewed as a cross-section of either a row or a column of pixels 120 of the image sensor 114. As such, in each of the foregoing equations ⟦*⟧ above, $q_{0,i}$ is the distance measured in the descending row direction between the point on the image sensor surface closest to the light emitter and the center of the closest photoactivated pixel and $q_{0,j}$ is a distance measured in the descending column direction between the point on the image sensor surface closest to the light emitter and the center of the closest photoactivated pixel.

Equations ⟦*⟧ enable designing the image sensor based on the desired observation space. For this, one can assume that $i_0=0$, $j_0=0$, $q_{0,i}=0$, $q_{0,j}=0$, d=0 (i.e., l=p, which is a good approximation for thin walls 118), and r−h=r (which is good for distances much greater than wall height) to obtain the approximation $$a_{i,j} = (p - h/r) \cdot (-p/2 + |i| \cdot p) \cdot (p - (h/r) \cdot (-p/2 + |j| \cdot p)).$$

From this follows directly that the number of pixels receiving light in i- or j-directions is proportional to 2·(r/h) and that the number of total pixels receiving light is proportional to 4·(r/h)². These numbers are independent of the pixel pitch, p, and thus, the height of the walls, h, has to be designed in accordance with the possible distances, r, of the light emitters from the image sensor for an image sensor with a given number of pixels. For example, it may be useful to design the image sensor so that at least nine pixels record light from the closest light emitter and no more than, e.g., 90% of the pixels record light from the furthest light emitter. In another example, it may be useful to design the image sensor so that at least 36 pixels record light from the closest light emitter and no more than, e.g., 1,000,000 pixels record light from the furthest light emitter. This means in some embodiments that the values for r are restricted approximately to being greater than 2 h and smaller than 1000 h, preferably greater than 3 h and smaller than 500 h.

In embodiments without a lens system between the object space and the image sensor, very small values for r (such as 2 h or 3 h) may be achieved by applying a very thin transparent layer (which has a thickness of 2 h or 3 h, respectively) above the image sensor. The light emitters may then be able to get as close to the image sensor as the transparent layer allows. In embodiments with a lens system (discussed in greater detail below), the confinements of the object space can define the confinements of the image space and by selecting the object space accordingly, the possible distances of the real images of the light emitters from the image sensor can be limited to, for example, 2 h or 3 h.

In different embodiments, the smallest value for r may be 5 h, 10 h, 100 h, or 500 h, corresponding to values of around 5 μm to up to 1,000 μm (depending on h). In embodiments without a lens system, larger values for r may be a consequence of a thicker layer that protects the image sensor better from the light emitters and the environment in which the light emitters are located (e.g., a liquid or a transparent substance). However, in embodiments with or without a lens system, the minimal r may be selected in such a way that at least a certain minimal number of pixels record light from each light emitter. The minimal number of pixels may be, for example, nine, 36, 100, 400, or 10,000.

Equations 〚*〛 describe the main component of the light profile measured by the image sensor from a single light emitter. As can be seen in the equations 〚*〛, the measured light intensity has its maximum value at pixel $p_{i_0,j_0}$ and the main component described by equations 〚*〛 decreases linearly by going away from the closest pixel $p_{i_0,j_0}$ into i and j directions (rows and columns of the image sensor).

Figure 4:
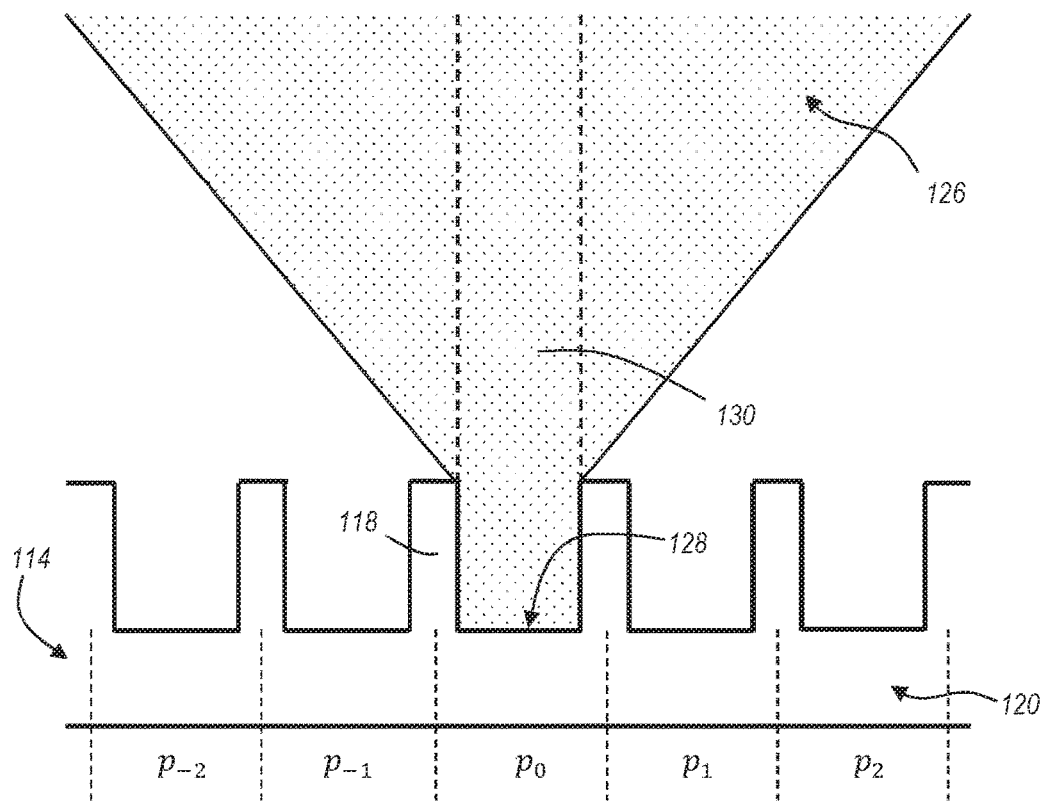
FIG. 4 illustrates an exemplary field of view for a pixel within the array of pixels comprising the image sensor, as limited by the associated structure.

The foregoing concept is illustrated in FIG. 4. As shown for representative pixel $p_0$, a field of view 126 for pixels 120 within the image sensor 114 is defined and limited by the height of the walls 118 and the side length 128 of a light receiving area of the pixels 120. Because some of the object space is precluded from the field of view 126, it is possible for a light profile to be generated for each light emitter that includes a subset of pixels within the array that receives light from the light emitter. In embodiments where the structure forms a regular grid, the corresponding light profile will be uniform in shape with the outer pixels measuring a lower light intensity than pixels located at the center of the light profile. The column 130 illustrates the part of the field of view 126 in which light emitters are recorded with a maximal intensity, and the closer the light emitter is to the limit of the field of view, the more the intensity is reduced such that a center or closest pixel can be identified. This demonstrates, at least in part, how the light profile for a given light emitter has an intensity gradient, and further, how a center or closest pixel can be determined and/or calculated.

With equations 〚*〛, it is already possible to determine the position of the light emitter 122 because the pixel which is closest to the single light emitter 122 (i.e., the pixel, $p_0$ through which the perpendicular line 124 through the plane of the image sensor 114 and the single light emitter 122 goes) indicates the position of the light emitter 122 in two directions and the distance r of the light emitter 122 from the image sensor 114 can be calculated with equations 〚*〛 using measured pixel values. For example, the closest pixel can be determined by identifying the pixel receiving the most light or by identifying the pixel that is in the middle of a pixel pair on the line $i=i_0$ or $j=j_0$, where each pixel of the pair records nearly the same amount of light but with light recording increasing in one direction for one of the two pixels and light recording decreasing in the same direction for the other one of the two pixels.

The distance r can be determined by identifying the distance between the closest pixel and the last pixel in either i or j direction that receives light from the light emitter. The condition $\tan(\alpha_1) < \tan(\alpha\_max)$ can be used to calculate r depending on the maximal number of pixels in one direction from the closest pixel which still receives light from the light emitter i_max. With the approximation that $Q_{0,i}=0$, it follows in the i-direction $$r = h \cdot (i\_max \cdot (p/l) + \tfrac{1}{2}).$$

It is interesting to note that this result for r is not affected by an attenuation of the light travelling from the light emitter 122 to the image sensor 114 as long as the furthest pixels that still receive measurable light are not changed.

In one embodiment, the light recording profile of a light emitter 122 may be determined more accurately, for example as described in more detail below, and r may be determined by using the measurements of pixels that are closer to the closest pixel and extrapolate the measurements to determine i_max (or j_max). In one or more other embodiments, the light profile of a light emitter may be determined purely through measurements, and this light profile may then be used to identify locations of light emitters in three-dimensional space with real measurements.

Therefore, the position of the single light emitter 122 can be determined in the three-dimensional object space using the equations 〚*〛.

This determination can be used to generate an image of the object space and determine the position of the single light emitter 122. As such, the foregoing may be, in some embodiments, sufficient for applications with single light emitters or clearly separated light emitters like, e.g., counting fluorescent objects in flow cytometry.

Theoretically and within an accuracy of around half a pixel pitch, it is possible to determine the distance r of a single light emitter 122 to the image sensor 114 by a measurement of a single pixel 120 assuming that the closest pixel and some other factors are known or have been determined. Also, the distance r can also be determined with the accuracy of around half a pixel pitch from the number of pixels that record light from the single light emitter and this calculation does not even depend on the brightness of the single light emitter.

However, it is possible to determine the distance r and the positions in the other two directions with sub-pixel accuracy (given by $q_{0,i}$ and $q_{0,j}$) by taking into account measurements from more than one pixel.

Generally, the measured light intensity $w_{i,j}$ of pixel i,j can be calculated as follows for a completely clear liquid (i.e., a liquid that does not absorb light):

$$w_{i,j} = w_0 \cdot \Omega_{i,j} \cdot a_{i,j}, \quad \text{〚**〛}$$

with $\Omega_{i,j}$ being the solid angle of the light emitter with respect to the light receiving area of pixel i,j and $w_0$ being a proportionality factor depending, for example, on the light intensity of the light emitter and on the measurement efficiency of the pixels.

The solid angle $\Omega_{i,j}$ can be calculated as known in the art. For example, the solid angle $\Omega_{i,j}$ of a light emitter with respect to the light receiving area of a pixel $p_{i,j}$ can be calculated using the formula for the solid angle $\Omega_{pyr}$ of a peak or a pyramid located in height h above the center of a rectangle with side lengths a and b:

$$\Omega_{pyr}(a, b, h) = 4 \arctan\left[ a \cdot \frac{b}{\left(2h \cdot \sqrt{(2h)^2 + a^2 + b^2}\right)} \right].$$

The solid angle of the light receiving area of a pixel $p_{i,j}$ that is not directly centered below the light emitter can now be determined using $\Omega_{pyr}$ and by calculating the solid angles for larger basis areas which form a pyramid with the light emitter centered and subtracting basis areas which do not belong to the light receiving area of the pixel $p_{i,j}$. This strategy is explained in an article titled "Solid Angle of a Rectangular Plate" by Richard J. Mathar (dated May 18, 2015, available online from the Max-Planck Institute of Astronomy). For $i \neq i_0$ and $j \neq j_0$, it is $$\Omega_{i,j} = \left(\frac{1}{4}\right) \cdot \left\{ \Omega_{pyr}\left[2 \cdot \left(\text{sgn}(i-i_0) \cdot q_{0,i} + \frac{l}{2} + |i-i_0| \cdot p\right), \right.\right.$$
$$2 \cdot \left(\text{sgn}(j-j_0) \cdot q_{0,j} + \frac{l}{2} + |j-j_0| \cdot p\right), r\right] -$$
$$\Omega_{pyr}\left[2 \cdot \left(\text{sgn}(i-i_0) \cdot q_{0,i} + \frac{l}{2} + |i-i_0| \cdot p + s_i\right),\right.$$
$$2 \cdot \left(\text{sgn}(j-j_0) \cdot q_{0,j} + \frac{l}{2} + |j-j_0| \cdot p\right), r\right] -$$
$$\Omega_{pyr}\left[2 \cdot \left(\text{sgn}(i-i_0) \cdot q_{0,i} + \frac{l}{2} + |i-i_0| \cdot p\right),\right.$$
$$2 \cdot \left(\text{sgn}(j-j_0) \cdot q_{0,j} + \frac{l}{2} + |j-j_0| \cdot p + s_j\right), r\right] +$$
$$\Omega_{pyr}\left[2 \cdot \left(\text{sgn}(i-i_0) \cdot q_{0,i} - \frac{l}{2} + |i-i_0| \cdot p + s_i\right),\right.$$
$$\left.\left. 2 \cdot \left(\text{sgn}(j-j_0) \cdot q_{0,j} - \frac{l}{2} + |j-j_0| \cdot p + s_j\right), r\right]\right\}.$$

$s_i$ and $s_j$ are the shadows calculated above:

$$s_i = h \cdot \frac{\left(\text{sgn}(i-i_0) \cdot q_{0,i} - \frac{l}{2} + |i-i_0| \cdot p\right)}{r-h}$$

$$s_j = h \cdot \frac{\left(\text{sgn}(j-j_0) \cdot q_{0,j} - \frac{l}{2} + |j-j_0| \cdot p\right)}{r-h}.$$

For $i = i_0$ and $j = j_0$ and $|q_{0,i}| \leq l/2$ and $|q_{0,j}| \leq l/2$, which is a good approximation for thin walls, it is $$\Omega_{i_0,j_0} = \left(\frac{1}{4}\right) \cdot \left\{ \Omega_{pyr}\left[2 \cdot \left(q_{0,i} + \frac{l}{2}\right), 2 \cdot \left(q_{0,j} + \frac{l}{2}\right), r\right] + \right.$$
$$\Omega_{pyr}\left[2 \cdot \left(-q_{0,i} + \frac{l}{2}\right), 2 \cdot \left(q_{0,j} + \frac{l}{2}\right), r\right] + \Omega_{pyr}\left[2 \cdot \left(q_{0,i} + \frac{l}{2}\right),\right.$$
$$\left. 2 \cdot \left(-q_{0,j} + \frac{l}{2}\right), r\right] + \Omega_{pyr}\left[2 \cdot \left(-q_{0,i} + \frac{l}{2}\right), 2 \cdot \left(-q_{0,j} + \frac{l}{2}\right), r\right]\right\}.$$

For $i \neq i_0$ and $j = j_0$ and $|q_{0,j}| \leq l/2$, it is $$\Omega_{i,j} = \left(\frac{1}{4}\right) \cdot \left\{ \Omega_{pyr}\left[2 \cdot \left(\text{sgn}(i-i_0) \cdot q_{0,i} + \frac{l}{2} + |i-i_0| \cdot p\right), 2 \cdot \left(q_{0,j} + \frac{l}{2}\right), r\right] - \right.$$
$$\Omega_{pyr}\left[2 \cdot \left(\text{sgn}(i-i_0) \cdot q_{0,i} + \frac{l}{2} + |i-i_0| \cdot p + s_i\right), 2 \cdot \left(q_{0,j} + \frac{l}{2}\right), r\right] +$$
$$\Omega_{pyr}\left[2 \cdot \left(\text{sgn}(i-i_0) \cdot q_{0,i} + \frac{l}{2} + |i-i_0| \cdot p\right), 2 \cdot \left(-q_{0,j} + \frac{l}{2}\right), r\right] -$$
$$\left.\Omega_{pyr}\left[2 \cdot \left(\text{sgn}(i-i_0) \cdot q_{0,i} - \frac{l}{2} + |i-i_0| \cdot p + s_i\right), 2 \cdot \left(-q_{0,j} + \frac{l}{2}\right), r\right]\right\}.$$

For $i = i_0$ and $j \neq j_0$ and $|q_{0,i}| \leq l/2$ it is $$\Omega_{i,j} = \left(\frac{1}{4}\right) \cdot \left\{ \Omega_{pyr}\left[2 \cdot \left(q_{0,i} + \frac{l}{2}\right), 2 \cdot \left(\text{sgn}(j-j_0) \cdot q_{0,j} + \frac{l}{2} + |j-j_0| \cdot p\right), r\right] - \right.$$
$$\Omega_{pyr}\left[2 \cdot \left(q_{0,i} + \frac{l}{2}\right), 2 \cdot \left(\text{sgn}(j-j_0) \cdot q_{0,j} - \frac{l}{2} + |j-j_0| \cdot p + s_j\right), r\right] +$$
$$\Omega_{pyr}\left[2 \cdot \left(-q_{0,i} + \frac{l}{2}\right), 2 \cdot \left(\text{sgn}(j-j_0) \cdot q_{0,j} + \frac{l}{2} + |j-j_0| \cdot p\right), r\right] -$$
$$\Omega_{pyr}\left[2 \cdot \left(-q_{0,i} + \frac{l}{2}\right),\right.$$
$$\left.\left. 2 \cdot \left(\text{sgn}(j-j_0) \cdot q_{0,j} - \frac{l}{2} + |j-j_0| \cdot p + s_j\right), r\right]\right\}.$$

The solid angle modifies the linear decay described by equations ⟦*⟧ so that the reduction of light intensities with distance from the closest pixel is faster than linear. The closest pixel of the image sensor to the light emitter can still be determined by, for example, identifying the pixel that records the greatest amount of light intensity. It is also possible to identify the closest pixel by determining the middle between pixel pairs that record the closest match of light intensities from all pixels and that are located on opposite sides of the closest pixel. Such pixel pairs are, e.g., $w_{i_0+m,j_0}$ and $w_{i_0-m,j_0}$ (for m=1 to i_max) or $w_{i_0,j_0+n}$ and $w_{i_0,j_0-n}$ (for n=1 to j_max). The closest point in the plane of the image sensor can be determined to a sub-pixel accuracy by determining $q_{0,i}$ and $q_{0,j}$ (which are the sub-pixel distances of the closest point in the plane of the image sensor to the center of the closest pixel) by taking into account the differences in recorded light of pixel pairs such as $w_{i_0+m,j_0}$ and $w_{i_0-m,j_0}$ (for m=1 to i_max) or $w_{i_0,j_0+n}$ and $w_{i_0,j_0-n}$ (for n=1 to j_max). An example calculation is also shown below. The measured light intensity values $w_{i,j}$ are discrete values so that the identification of i_max or j_max may be still possible with a high degree of accuracy in the real world and these values may be used to determine the distance r from the plane of the image sensor. It should be added that $\Omega_{i,j}$ depends also on r so that r cannot be easily determined analytically for any given pixels that receive light from the light emitter. However, it is still possible to determine r in a numerical way from the measured $w_{i,j}$ for any given pixel that receives light assuming that the closest pixel and $w_0$ has been determined. It is also possible to use equation ⟦*⟧ to calculate light profiles for different values of r and then fit the measured light profiles to the calculated light profiles to determine r to a pre-determined accuracy.

It may be added that a more accurate expression for $w_{i,j}$ may require further correction factors compared to equation ⟦⟧ which take into account, e.g., light recording efficiency of pixels for different incident angles of light. However, such correction factors would be universal for all pixels and can easily be incorporated in equation ⟦⟧. It may also possible to incorporate measured correction factors in equation ⟦⟧. The equation ⟦⟧ also assumes that the light emitter emits light in all directions homogeneously (i.e., light is emitted in all directions with the same intensity). It is also possible to take into account inhomogeneous light emission by using the measured light intensity values from a plurality of pixels and fit them to a known inhomogeneous light emission profile of the light emitter.

Assuming that the light from the light emitter is at least recorded by nine pixels (one central pixel and the next neighbor pixels), and assuming $|q_{0,i_0}| \leq l/2$ and $|q_{0,j_0}| \leq l/2$ (which is a good approximation for thin walls) then $w_0$ may be determined from $w_{i_0,j_0}$ by using $$w_0 = w_{i_0,j_0}/(l^2 \cdot \Omega_{i_0,j_0}).$$

$q_{0,j}$ can be determined for example from $w_{0,1}$ and $w_{0,-1}$ and $q_{0,i}$ from $w_{1,0}$ and $w_{-1,0}$. With the approximation $|q_{0,i_0}|<1/2$ and $|q_{0,j_0}|<1/2$ and assuming for simplicity that $i_0=0$ and $j_0=0$, it follows:

$$q_{0,j} = (h/2l) \cdot (a_{0,-1} - a_{0,1})$$
$$= (h \cdot l \cdot \Omega_{0,0}/2w_{0,0}) \cdot (w_{0,-1} - w_{0,1}) \text{ and}$$

$$q_{0,i} = (h/2l) \cdot (a_{-1,0} - a_{1,0})$$
$$= (h \cdot l \cdot \Omega_{0,0}/2w_{0,0}) \cdot (w_{-1,0} - w_{1,0}).$$

It is thus possible to determine the position of a single light emitter in two dimensions to a sub-pixel accuracy after r has been determined with a high accuracy from, e.g., identification of i_max (using formula above). The sub-pixel distances between the closest point in the image sensor plane to the light emitter and the center of the closest pixel, $q_{0,i}$ and $q_{0,j}$, may also be determined from the difference of other pixel pairs such as $w_{0,-2}-w_{0,2}$ and $w_{-2,0}-w_{2,0}$.

The distance r can also be determined in a different way from any one of the measurements $w_{1,0}$, $w_{0,1}$, or $w_{1,1}$ using the equations 〚 * 〛 and 〚 ** 〛. For $w_{1,0}$, it follows:

$$w_{1,0} = w_0 \cdot \Omega_{1,0} \cdot \left[l - h \cdot \frac{\left(q_{0,i} - \frac{l}{2} + p\right)}{r-h}\right] \cdot l$$

$$= \left[w_{0,0} \cdot \frac{\Omega_{1,0}}{\Omega_{0,0}} \cdot l\right] \cdot \left[l - h \cdot \frac{\left(q_{0,i} - \frac{l}{2} + p\right)}{r-h}\right]$$

$$= \left[w_{0,0} \cdot \frac{\Omega_{1,0}}{\Omega_{0,0}} \cdot l\right] \cdot \left[l - h \cdot \frac{\left(\left(h \cdot l \cdot \frac{\Omega_{0,0}}{2w_{0,0}}\right) \cdot (w_{-1,0} - w_{1,0}) - \frac{l}{2} + p\right)}{r-h}\right].$$

The left side is a measurable quantity and the right side depends in a complicated way on the distance r and known or measurable quantities: the dependency is not only through the r appearing in the equation but also through the solid angles which depend also on r. It is analytically difficult, or improbable, to invert the function and express r in terms of known or measurable quantities but the inversion is possible numerically and can be used to determine r from known quantities and quantities that have been measured (after they have been measured).

Thus, it is also possible to determine the distance r of the light emitter from the image sensor with a sub-pixel accuracy using the measurements $w_{0,0}$, $w_{1,0}$, and $w_{-1,0}$. It is also possible to use measurements from pixels that are further away from the closest pixel to determine r. It is also possible to determine r in multiple different ways and calculate r with a higher accuracy using statistical methods such as averaging.

To determine the brightness of the light emitter, $w_0$ may be calculated using, e.g., the measurement $w_{i_0,j_0}$ and relate $w_0$ to the brightness. This can be achieved based on theoretical calculations (taking into account light measurement efficiency of the pixels and brightness of the single light emitter) or by calibration with known light emitters at known distances from the image sensor. Absorption of light travelling from the light emitter through a medium to the pixels may also be taken into account by adding a correction factor to the equation 〚 ** 〛. The correction factor may depend on the distance that the light travels through the medium and may decay exponentially with this distance.

In any case, equations 〚 * 〛 and 〚 ** 〛 allow for the determination of the precise position of the single light emitter in the object space and with additional information also the brightness of the single light emitter. Usually, many pixels will record light from the single light emitter and measurements from other pixels can be used to determine the position and brightness with a higher accuracy by, e.g., determining the average value of r, average(r). In an example, light from the light emitter may be measured by 10,000 pixels (in an area of 100×100 pixels) and r may be determined for all 100 pixels of a row of the closest pixel (50 to –i-direction and 50 to i-direction) and for all 100 pixels of a column of the closest pixel. The 200 values for r can then be averaged to obtain a more accurate value of r. Similarly, the closest pixel (or the two or four closest pixels if the light emitter is above a boundary of a pixel) may be determined not only by identifying the pixel that records the maximum light intensity but also by extrapolating the increase of recorded light intensity from pixels close to the closest pixel to determine the column and row containing $i_0$ and $j_0$ and thus $i_0$ and $j_0$ themselves. It is also possible to use measured values of pixels that are located outside the row or column of the closest pixel to determine the parameters of the light emitter with a high accuracy.

Determining Positions and/or Brightness of Multiple Light Emitters

In some embodiments, a plurality of light emitters is present in the object space, and some of the light emitters may have overlapping light profiles. Using prior systems/methods, it may be difficult to determine the central or closest pixel for each light emitter (and thereby the distance r), reducing the accuracy by which positions of the light emitters are determined. By implementing the systems disclosed herein, an accurate determination of multiple light emitters is enabled, even when these light emitters have overlapping light profiles. For more than a single light emitter in object space, the following exemplary methods can be performed to determine the position and brightness, sequentially, for each one of the light emitters present in the object space that is observed.

In one embodiment, a method for determining the position of light emitters includes the following steps:
1. Determining one pixel (or two or four) at $i_0$, $j_0$ at which a local maximum of light intensity is measured from a light emitter.
2. Calculating the distance r of the light emitter from the image sensor and identifying the point of the image sensor that is closest to the light emitter, for example, by using equations 〚 * 〛 and 〚 ** 〛, optionally further determining the brightness of the light emitter using further input.
3. Subtracting the light profile of the light emitter from the measured light intensities of the image sensor, for example, by using equations 〚 * 〛 and 〚 ** 〛.
4. Repeating steps 1 to 3 for the next local maximum of light intensity to determine all parameters for the next light emitter until no further local maximum can be determined.
5. Constructing a complete image of the three-dimensional observation space with all its light emitters using the determined parameters for the light emitters. This image may be used for automated analysis or for creating an image for displaying to a user.

Regarding step 2, different light emitter configurations may be distinguished. In one instance, it may be possible that each pixel records only light from one light emitter, that is, there is no overlap of light from two different light emitters at one pixel. In such a case, the light emitters can be treated separately as single light emitters.

In another instance, there may be an intersection of the set of pixels recording light from one light emitter and the set of pixels recording light from another light emitter, but the intersection is relatively small so that it can be identified and the parameters for the two light emitters can be determined from pixels that record light from only one of the two light emitters (i.e., pixels not in the intersection).

In some instances, the intersection of sets of pixels recording light from two different light emitters is large; that is, it is a substantial portion of two sets, and the two sets have a similar size. This means that the two light emitters are close to each other (and have a similar distance r to the image sensor). Some exemplary diagrams illustrating particular examples of such instances are shown in FIGS. 5-8. Each of FIGS. 5-8 illustrate a side view of two light emitters and corresponding cones of light recorded by pixels of the image sensor and the resulting combined light intensity profiles of the two light emitters. The combined light intensity profiles include three regions: region one consists of the pixels that record light only from the first light emitter, region two consists of pixels that record light from the first and second light emitters, and region three records light from only the second light emitter. For simplicity, all light intensity illustrations assume that the solid angle is constant for all pixels so that the changes in light intensity are linear, as given by the equations ]**] for the pixel area that records light.

Figure 5:
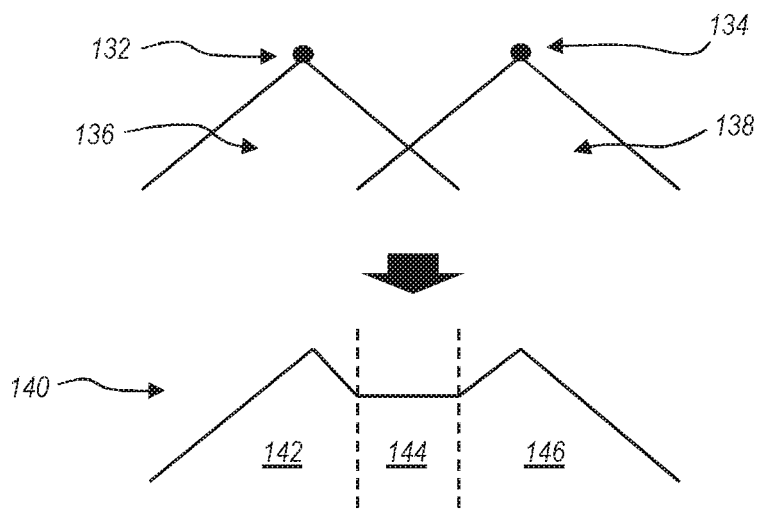
FIG. 5 is a diagram illustrating a side view of two light emitters and corresponding cones of light recorded by pixels of the image sensor and the resultant exemplary combined light intensity profile of the two light emitters.

For example, FIG. 5 illustrates a first light emitter 132 that is near a second light emitter 134, and each light emitter 132, 134 is shown with a corresponding cone of light 136, 138. Additionally, the combined light intensity profile 140 is shown, as determined from the photoactivated pixels receiving light from the light emitters 132, 134. For simplicity, it is assumed that the two light emitters 132, 134 are located along a row of pixels of the image sensor and the light intensities are shown for this row of pixels. This applies also to the following illustrated examples. As provided above, the light intensity profile 140 includes a first region 142, a second region 144, and a third region 146. The first region 142 corresponds to a light intensity profile recorded by pixels receiving light only from the first light emitter 132. The second region 144 corresponds to the combined light intensity profile recorded by pixels receiving light from both the first 132 and second 134 light emitters. The third region 146 corresponds to a light intensity profile recorded by pixels receiving light only from the second light emitter 132. In the example of FIG. 5, the parameters for the two light emitters 132, 134 can be determined from regions one and three, respectively.

Figure 6:
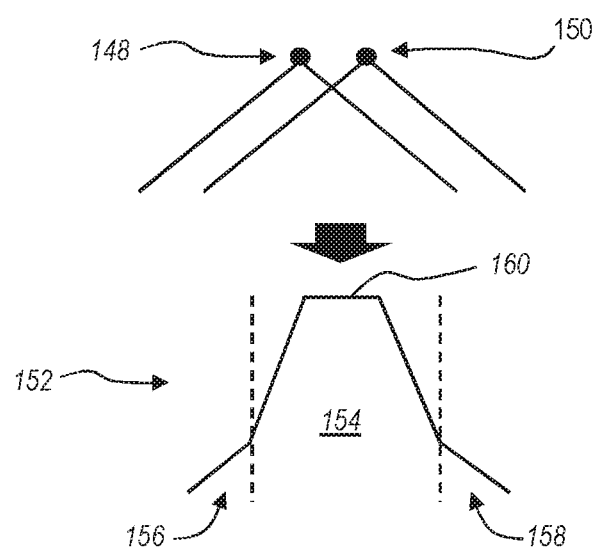
FIG. 6 is another diagram illustrating a side view of two light emitters and corresponding cones of light recorded by pixels of the image sensor and the resultant exemplary combined light intensity profile of the two light emitters.

FIG. 6 illustrates an example where the proximity of two light emitters 148, 150 create a combined light intensity profile 152 where region two 154 becomes large. It is still possible to identify the first 156 and third 158 region to determine the parameters for the two light emitters 148, 150, but it is also possible to determine the parameters from region two 154 by assuming that the two light emitters 148, 150 are equally bright (otherwise, there would not be a horizontal line 160, but a tilted line, defining the apex of the second region 154) at the same distance (otherwise, the first region 156 and the third region 158 would not have the same size) and at positions over the image sensor that are identified by the beginning and end of the horizontal line 160. If the foregoing assumptions are not met, it may still be possible to determine the parameters for each light emitter using a combination of method steps disclosed herein.

Figure 7:
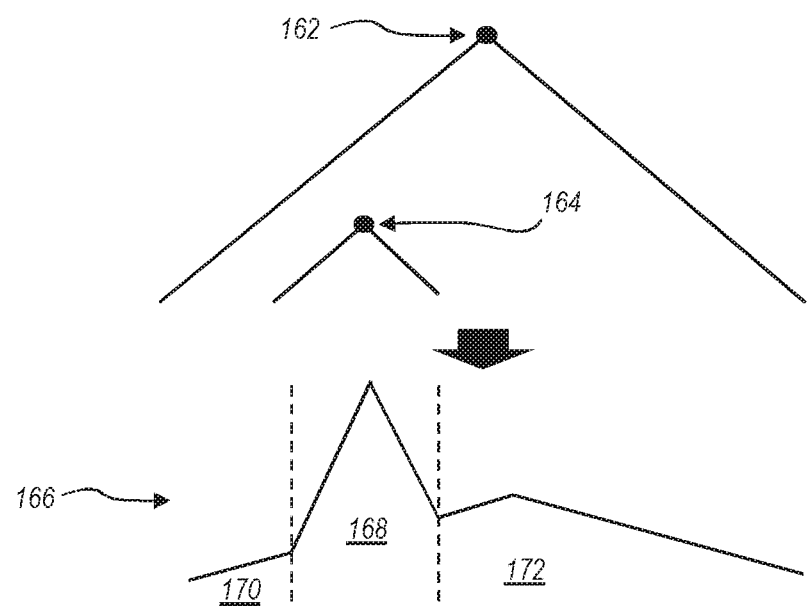
FIG. 7 is yet another diagram illustrating a side view of two light emitters and corresponding cones of light recorded by pixels of the image sensor and the resultant exemplary combined light intensity profile of the two light emitters.

In another example, illustrated in FIG. 7, the intersection of sets of pixels recording light from two different light emitters 162, 164 is large (i.e., the second region 168 of light intensity profile 166 is large), and the first 170 and third 172 regions have different sizes. This means that the two light emitters 162, 164 have closest pixels that are close to each other but are also located at different distances to the image sensor.

It should be appreciated that in some embodiments, the total light intensity measured by the image sensor from a light emitter can be similar and may not depend much on the distance r of the light emitter. One reason for this may be that the angle of the light cone measured by the image sensor remains the same (i.e., does not increase when the light emitter gets closer to the image sensor, in contrast to a conventional lens-based system). From this follows that light from a light emitter closer to the image sensor is received by less pixels but will be recorded in the less pixels with a larger intensity. In contrast to this, a light emitter that is far away from the image sensor is seen by more pixels, but each pixel records a smaller amount of light from the light emitter.

Accordingly, assuming that the image sensor receives an equivalent total light intensity from each light emitter, the total light intensity associated with the light emitter farther away from the image sensor is spread out among a larger number of pixels compared to the light emitter closer to the image sensor. With continued reference to FIG. 7, this result can be exemplified by the disparate slopes and peaks of light intensity shown in the combined light intensity profile 166. Each pixel receiving light from the light emitter 162 farther away from the image sensor registers a light intensity that is incrementally different (greater or lesser) than a neighboring pixel, whereas each pixel receiving light from the light emitter 164 closer to the image sensor registers a light intensity that is (comparatively) much different (greater or lesser) than a neighboring pixel. This is because, as stated above, the sum of light intensities for all pixels receiving light from each light emitter 162, 164 is equal, and spreading a defined light intensity over a larger number of pixels results in an average light intensity per pixel that is less than the average light intensity per pixel when spreading the same defined light intensity over a smaller number of pixels.

As shown in FIG. 7, it is possible to first determine the parameters for the light emitter 162 that has a larger distance to the image sensor and then subtract the profile of this light emitter 162 from the measured values. Following this, the parameters for the closer light emitter 164 can be determined. However, it is also possible to first determine the parameters from the light emitter 164 that is closer to the image sensor and subtract its light profile from the measured values. The second method may, in some instances, be better because the closer light emitter 164 is more acutely defined (less pixels have to be taken into account and the light intensities are larger), and the local maximum can be better identified. So, it may be generally better to identify first the light emitters that are close to the image sensor. In such a procedure, it should be noted that generally for a single light emitter, the absolute value of the slope in an i-direction is the same as the absolute value in the −i-direction (but the sign is different). Thus, calculating half of the difference of the absolute value of the slope in the i-direction and the −i-direction gives an approximation of a true slope of the closer light emitter without a contribution from the light emitter that is further away (this assumes that the contribution of the light emitter farther away to the slope is constant).

Figure 8:
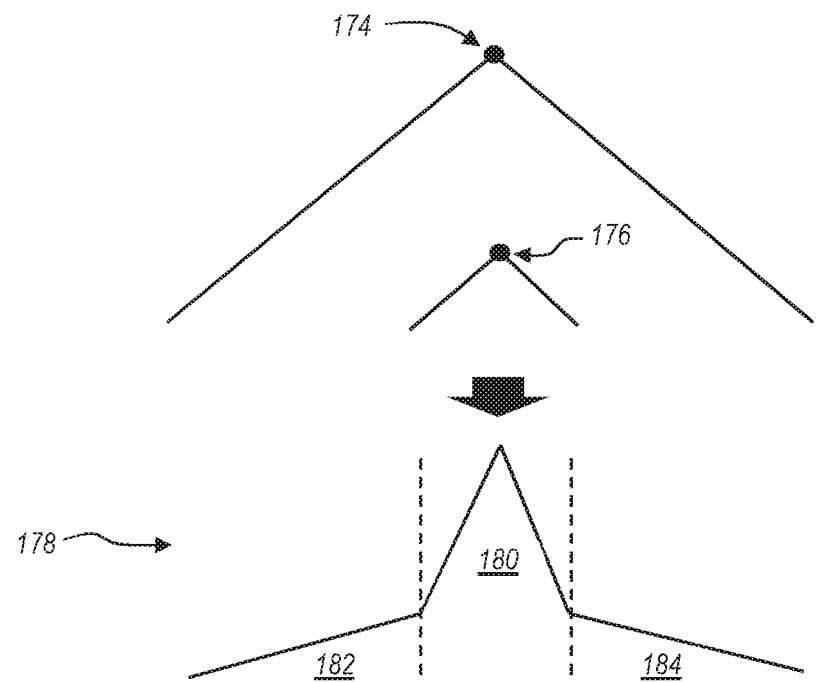
FIG. 8 is still another diagram illustrating a side view of two light emitters and corresponding cones of light recorded by pixels of the image sensor and the resultant exemplary combined light intensity profile of the two light emitters.

Referring now to FIG. 8—which is a special case because the light emitters 174, 176 are on the same perpendicular line in the two-dimensional cross-section shown in FIG. 8 (as determined by the combined light intensity profile 178 having a single peak centered on the second region 180 and flanked by equal, but opposite, first 182 and third 184 regions)—identifying the different slopes in i-direction and the −i-direction indicates that two light emitters 174, 176 are present that have the same closest pixel but different distances to the image sensor. In such an instance, it may be better to first determine the parameters for the light emitter 174 that is further away from the image sensor using the measurements of pixels that record only light from this light emitter, subtract the light profile of this light emitter, and then determine the parameters for the closer light emitter 176 using the corrected measurement values.

In some embodiments, particularly those similar to FIG. 8, the light intensity profiles for each of the overlapping light emitters 174, 176 may be determined, as above, where measurements from pixels in the first 182 and/or third 184 regions are used to determine the position of the farther light emitter 174. The position of this light emitter 174 can then be used to calculate a theoretical light intensity profile for the light emitter, which values can be subtracted from the combined light intensity profile 178 to yield the light intensity profile for the closer light emitter 176.

It should be appreciated that when the two light emitters are getting as close as the pixel pitch of the image sensor, they may not be resolved or differentiated from each other because the resolution of the two light emitters is less than the resolution of a single light emitter. It may be possible to determine that two light emitters are present—owing to the combined light intensity received by pixels being double that of a single light emitter—but it would be involved to accurately determine the position of each light emitter.

Three or more light emitters with overlapping light profiles can be identified by determining the different regions that record light from one, two, and three light emitters and using them to determine the parameters for each one of the individual light emitters. Similarly, four or more light emitters can be identified by determining the different light regions that record light from each of the four or more light emitters and using them to determine the parameters for each one of the individual light emitters.

If there is a line of light emitters that are so close that the distance between the light emitters cannot be resolved, it is possible to locate the line of light emitters in object space in the following way: the line of light emitters can be identified by a line of maximum light intensity measured by pixels of the image sensor (light intensity is lower perpendicularly to the line) and for the distance information, also the values of pixels that are located perpendicularly to the line of maximum light intensity may be used.

Calculating the Resolution of an Exemplary Image Sensor

In some embodiments, the physical properties of the image sensor assembly (i.e., of the image sensor and the associated structure) can be used to determine a resolution for the corresponding assembly. This can include, for example, calculating the parallel and/or perpendicular resolution of an image sensor assembly.

In one or more embodiments, the parallel resolution can be calculated. For exemplary purposes, the parallel resolution can be calculated based on FIG. 6. For this, the two light emitters can be assumed to be very close up to the pixel pitch, p. In this case, it is possible to determine that there are two different, but close, light emitters of similar brightness at similar distance to the image sensor (otherwise the light intensity would not be equal for a line of pixels). The number of pixels that record maximal light intensity can be used to determine the parallel distance between the two light emitters and this can be done up to p. Therefore, the parallel resolution is equal to p. The distance of the two light emitters can still be determined from, e.g., the number of pixels recording light from the two light emitters or from the slope of the light intensity in the i, −i, j, and −j-direction. It should be noted that for a single light emitter, it can be trivial to obtain a sub-pixel-pitch resolution by taking into account different measurements in the i- and −i-directions and in the j- and −j-directions (see above). Such calculations are also possible for two light emitters, but it can become more computationally complex and preferably further interfering light emitters (which can cause different measurements in the plus and minus directions) are absent so that the parallel resolution of two light emitters can be taken to be approximately p.

In one or more embodiments, the perpendicular resolution can be calculated. For exemplary purposes, the perpendicular resolution can be calculated based, for example, FIG. 8. As the two light emitters are getting closer and closer, the number of pixels recording only light from the light emitter will become smaller and smaller. The light cone of both light emitters (i.e., the light recorded by pixels in one direction) has the same angle $\alpha\_max$, which is $\tan(\alpha\_max)=l/h$. A difference D of how far the light cones can be seen by the image sensor is equal to the perpendicular distance between the light emitters times (l/h) because $$D=D2-D1=(r+\Delta)\cdot\tan(a\_max)-r\cdot\tan(a\_max)=\Delta\cdot\tan(a\_max)=\Delta\cdot(1/h).$$

If the minimal value for D is taken to be p (i.e., D>p) so that at least one line of pixels in all four directions can be identified that receives only light from the light emitter that is further away, then the perpendicular resolution is p·(h/l) (because $\Delta\cdot(l/h)=D>p$). Therefore, the perpendicular resolution of two light emitters can be taken to be p·(h/l).

In the following, two example applications will be described in more detail. In a first exemplary application, a relatively large object space can be monitored for rare light emitters (as may be the case for counting applications in flow cytometry or other, similar tasks). For this, the image sensor is relatively large and has relatively large pixels: p=10 μm, l=9 μm, the image sensor chip is 30 mm×30 mm—giving a resolution of 9 mp (mega pixels). The object space is assumed to be as large as the image sensor chip and the perpendicular size is limited to be between 1 mm and 10 mm. Some or all of these values may also be completely different. However, for such values, h=20 μm is a sensible value.

From this follows that light from a single light emitter as close as possible will be recorded by pixels inside a square of 0.9 mm side length, that is, by roughly 8,000 pixels. Light from a single emitter as far away as possible will be recorded by pixels inside a square of 9 mm side length, that is, by roughly 0.8 million pixels. In some embodiments, it is possible to increase the number of pixels that record light from the light emitter by decreasing h.

In the second application, a high resolution will be achieved as may be done for microscopic applications. For this, the image sensor is relatively small and has small pixels: p=1.1 μm, l=1 μm, the image sensor chip is 5.5 mm×5.5 mm, giving a resolution of 25 mp (mega pixels). The object space is assumed to be as large as the image sensor chip and the perpendicular size is limited to be between 20 μm and 50 μm. For such values, h=2 μm is a sensible value. From this follows that light from a single light emitter that is as close as possible to the image sensor will be recorded by pixels inside a square of 20 μm side length, that is, by roughly 320 pixels. Light from a single emitter as far away as possible will be recorded by pixels inside a square of 50 μm side length, that is, by roughly 2,000 pixels.

It should be appreciated that, in general, the resolution of the image sensor assembly can be adjustable at least within a direction perpendicular to the surface of the image sensor based on a combination of one or more of the pixel pitch of the image sensor, the height of the structure, and the inverse of the side length of a light-sensitive area of the pixels.

Additional Exemplary Image Sensor Assemblies

The image sensor assembly of FIGS. 2-4 is an example of a more general concept that provides wells or a structure that define a certain field of view for each pixel. It may also be possible to limit the field of view to light that is perpendicular to the image sensor (i.e., the field of view of each pixel is as large as the pixel itself and has a zero opening angle), but this would reduce the amount of light that is recorded from each light emitter, especially the ones that are further away from the image sensor, and would not make it possible to determine the distance of the light emitter from the image sensor (i.e., not without an additional image sensor that is perpendicular to the image sensor). Further, some of the advantages disclosed above would be reduced and/or eliminated.

Figure 9:
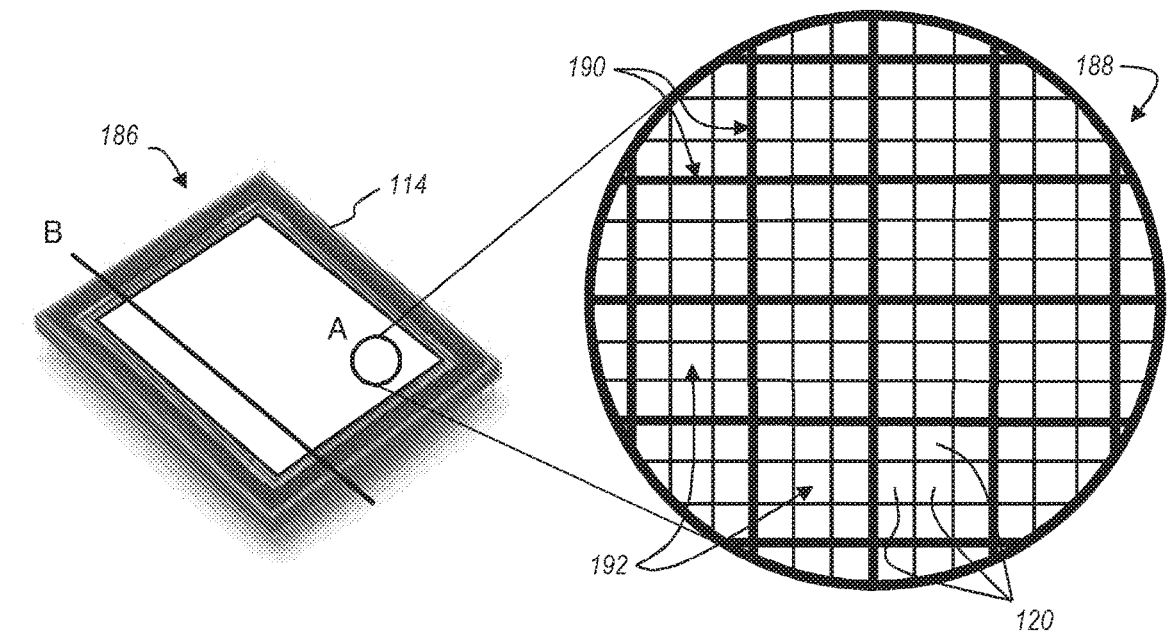
FIG. 9 illustrates a schematic of an image sensor having a structure associated therewith such that the structure surrounds 3-by-3 groups of pixels, forming a regular grid.
Figure 10:
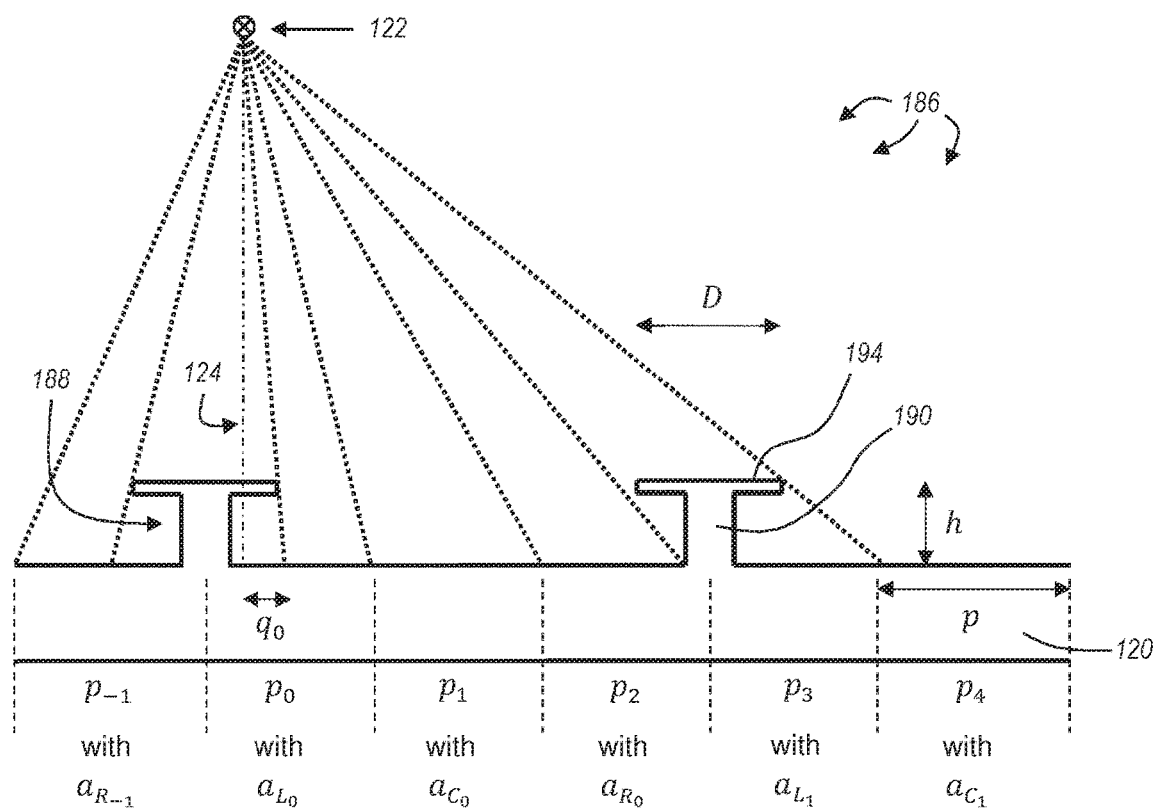
FIG. 10 is a cross-sectional side view of the image sensor and associated structure of FIG. 9, showing a light emitter disposed a height above the image sensor.

In an additional embodiment illustrated in FIGS. 9 and 10, an image sensor assembly 186 can include an image sensor 114 comprising an array of pixels 120 arranged in rows and columns. The image sensor 114 can be associated with a structure 188 associated with, and extending a height away from, the surface of the image sensor 114. The structure 188 can include a plurality of walls 190 disposed on the pixel boundaries of each pixel (not shown) or a set of pixels 192. For example, as shown in FIG. 9, the walls 190 can surround a group of neighboring pixels, such as every group of 3×3 pixels. It should be appreciated that although a 3×3 group of pixels is illustrated, any number of pixels can comprise a group of pixels. For example, the wall 190 can surround a 1×2, 2×1, 2×2, 2×3, 3×2, 3×4, 4×3, 4×4, or larger group of neighboring pixels according to a desired resolution or application.

In the cross-section illustrated in FIG. 10, the walls 190 can include a well-defined horizontal structure 194 on top of the walls 190, forming a T-profile in cross-section. Such walls 190 and horizontal structure 194 may be used to further restrict the angle of view of the pixels without requiring an increase in the height of the wall 190. For example, it may be inefficient to manufacture walls that are ten times higher than the pixel pitch of the image sensor. However, such a wall height may be desired to allow for monitoring light emitters that are quite far away from the image sensor. Instead of using the desired high walls, it may be better or preferable to use walls that are, for example, as high as the pixel pitch of the image sensor and which have a horizontal structure on top that further reduces the opening. As a result, the opening angle of each pixel is reduced, and therefore, each light emitter will be seen by less pixels, which again allows for an easier distinction of light emitters that are far away from the sensor.

The light profile of such walls may be determined analytically, too. Compared to walls without a horizontal structure, the light profile of walls with a T-profile (in cross-section) may be changed in such a way that the difference in light intensity recorded by the closest pixel and certain pixels close to it is larger.

With reference to the exemplary embodiment of FIGS. 9 and 10, the light profile of a light emitter 122 can be calculated for such a wall configuration. It follows for the three different pixels per group of pixels in one direction: for the left pixel of each group of three pixels in the positive i-direction, it is $$a_{L_i} = p - D/2 - s_{L_i} \text{ with}$$

$$s_{L_i} = h \cdot \left(q_{L_0} + \frac{p}{2} + \frac{D}{2} + (3i-1)\right) \cdot p/(r-h),$$

with D being the thickness of the horizontal structure (which is symmetrically placed on top of the wall), for $q_{L_0} \leq p - D/2$ and $s_{L_i}$ being greater than $-5p/2$ and less than $p/2$. Here, the closest point of the image sensor (not counting the walls) is assumed to be in the center of a left pixel and the index i identifies the number of pixel groups starting from the closest pixel group (and not the number of pixels). For simplicity, it is assumed that the complete pixel area is able to record light (i.e., l=p).

For the center pixel of each group of three pixels in the positive i-direction, it is $$a_{c_i} = p - s_{c_i} \text{ with}$$

$$s_{c_i} = h \cdot (q_{L_0} + p/2 + D/2 + (3i-1) \cdot p)/(r-h) - (p-D/2),$$

for $h \cdot (q_{L_0} + p/2 + D/2 + (3i-1) \cdot p)/(r-h) \geq p - D/2$ and for $h \cdot (q_{L_0} + p/2 + D/2 + (3i-1) \cdot p)/(r-h) - (p-D/2) \leq p$.

For the right pixel of each group of three pixels in the positive i-direction, it is $$a_{R_i} = p - s_{R_i} \text{ with}$$

$$s_{R_i} = h \cdot (q_{L_0} + p/2 + D/2 + (3i-1) \cdot p)/(r-h) - (p-D/2) - p,$$

for $h \cdot (q_{L_0} + p/2 + D/2 + (3i-1) \cdot p)/(r-h) \geq p - D/2$ and for $h \cdot (q_{L_0} + p/2 + D/2 + (3i-1) \cdot p)/(r-h) - 2p + D/2 \leq p - D/2$.

For such an embodiment, the light profile may be better able to identify the closest pixel because the first left pixel (i.e., the left pixel of the first group of three pixels in the i-direction starting from the group of the closest pixel) already has a very much reduced light intensity because the horizontal structure 194 casts a relatively large shadow on this pixel. In an example, D may be equal to l (so that each pixel to the left and right of the wall has an area of l/2 in one direction that is covered by the horizontal structure), and a light emitter that is very far away and located above a left pixel of a group of three pixels will be recorded with full intensity by the center pixel of the closest group, with slightly more or slightly less than half of the full intensity by the left pixel (which is the closest pixel) and with more than half of the full intensity by the right pixel (because light can be measured in an area that is directly under the horizontal structure). This light profile allows for the determination of the closest pixel of the group.

Furthermore, the closest pixel can be identified by the light intensity of the next left pixel to the right which records less than half of the full intensity while the center pixel of this group records the full intensity and the right pixel of this group records more than half of the full intensity. The next groups of three pixels to the right (e.g., in the positive i-direction) will show a light profile in which the light intensity recorded by the left pixels of each group will quickly be reduced to zero while the center and the right pixel of each group will be reduced to zero much slower (the right pixel being the last pixel that records any light from the light emitter). The faster decay of the light intensity of the left pixels going to the positive i-direction and the equally faster decay of the light intensity of the right pixels going to the negative i-direction may allow for an easier identification of the closest pixel for light emitters that are far away from the image sensor.

It is also possible to calculate the distance r from the image sensor for each one of the three pixel types separately (e.g., by determining the furthest pixel of each type—left pixels, center pixels, and right pixels—that still records light) to confirm that the values for r are consistent. Alternatively, it may be possible select only one pixel type for calculating the r value based on the range of r.

In further embodiments, the wells created by the structure associated with the image sensor may have a different shape and/or cross section other than that disclosed above. For example, the well structure can be arcuate (e.g., round like a circle) or polygonal (e.g., hexagonal). The wells may also be associated with microlenses disposed atop of the wells to increase the field of view or to focus light onto a light sensitive area of the pixels.

In some embodiments, the pixels may also have optical filters to limit the light recorded at the pixels to one or more certain wavelength ranges. The optical filter material may be located inside the wells, optionally up to the height of the walls. In such cases, the above calculations may be modified to take into account refraction of light at the optical filter material. The optical filter material may also be located above the wells.

For embodiments where the image sensor has one optical filter in all wells, the image sensor may be quickly exchangeable with another image sensor having a different optical filter to be able to make measurements in different wavelength ranges.

In one or more embodiments, the image sensor may have different optical filter material in different wells. The different optical filter material may be arranged in a color filter array, and the color filter array may be a Bayer pattern, which is often used for image sensors in digital cameras. Such an image sensor allows for recording of colored images but may result in the resolution being lower.

In some embodiments, 2 or more image sensors can be used to record light from the same object space at the same time. The image sensors may, e.g., be positioned in front of the object space, behind it, and/or at sides thereof. The plurality of image sensors may be positioned at defined angles with respect to each other, such as, e.g., orthogonally to each other and such that the object space can be illuminated from one side (e.g., above) with excitation light. Each of the plurality of image sensors may have a different optical filter material to provide color images or they may be used to increase the resolution of the system, especially if the object space is large and contains quite a lot of light emitters. In some embodiments, a plurality of image sensors is positioned serially—imaging a different section of object space—to cover a larger object space.

The image sensor may also be movable with respect to the object space so that the object space can be imaged from different points of view in order to increase resolution. This can be particularly advantageous if a lot of light emitters are present in the object space. In an embodiment, the image sensor may be moved by tilting the image sensor with respect to the object space so the field of view of the pixels is changed. In a further embodiment, the image sensor may be moved along a portion of a sphere to record light from the object space from different directions. In still a further embodiment, the image sensor can be translated in a z-direction with respect to the object space, effectively growing, shrinking, or translating the object space.

The image sensor can also be used to observe a point (or very small region) in the object space. For this, a single converging lens, possibly a Fresnel lens, may be placed on top of the image sensor to cover all wells. The wells may be deep or have a very small field of view so that only perpendicular light from the converging lens is recorded by the pixels. The perpendicular light is light that is coming from the focal point of the converging lens so that light from other regions of the object space is effectively filtered out.

An image sensor as described above may also be used for recording light going through the sample (e.g., light that is not emitted by an emitter in the object space). The light going through the sample may be collimated light (perpendicular to the image sensor surface) as it may be used in projection microscopy. However, in contrast to projection microscopy, the overlapping field of view of different pixels of the image sensor allow for a determination of a distance of objects from the image sensor although it may be better to use pixels with a small field of view (i.e., relatively high walls that are at least as large as the pixel pitch). Alternatively, the light may be considered as being emitted by one or more light emitters in the object space and a light intensity profile may be calculated or measured for the one or more light emitters in combination with a structure located between the one or more light emitters and the image sensor. The structure may be opaque so that it blocks a portion of the light that would otherwise be recorded by pixels of the image sensor. In an example, the structure may be a very thin square structure with a side length of the pixel pitch and oriented in parallel to the surface of the image sensor. Such a light intensity profile may then be used as a basis to identify arbitrary shapes of structures blocking light from one or more light emitters that are farther away from the image sensor than the arbitrary structures.

In some embodiments, the image sensor assembly includes or is associated with a backside illuminated chip for increasing a light sensitive area of each pixel or each set of pixels. Additionally, or alternatively, the image sensor assembly can be associated with a transparent material disposed in the space between the structure and the image sensor. In some embodiments, the transparent material is disposed above the structure and/or between the structure and the image sensor. This can be beneficial for protecting the image sensor assembly in implementations where the sample includes liquids or chemicals that are directly associated with the image sensor (e.g., partially submerging the image sensor assembly in the sample).

Image Sensors Associated with Lens Systems

While the image sensors described above do not necessarily have a limited depth of field like a standard camera system, it may nonetheless be difficult to identify and/or position distant light emitter if they are positioned too far away from the image sensor. One reason for this may be that the change of light intensity recorded by different pixels from a distant light emitter is small, making it difficult to identify the closest pixel that records the greatest amount of light. This results in a loss of fidelity and/or increased difficulty when determining the position of the light emitter with respect to the co-planar directions of the image sensor. In some instances, this can even result in the inability to determine the exact number of light emitters within the object space. Even if a closest pixel (e.g., local maximum of light intensity) can be identified, it may be difficult to confidently determine the distance of the light emitter from the image sensor owing to the slow decay of light intensity measured by the surrounding pixels. An additional complicating factor includes situations where the light emitters have overlapping light profiles to the extent that the pixels are receiving light from more than one light emitter.

At least some of the foregoing problems may be addressed by moving the image sensor into closer proximity with the light emitters. However, in some instances, it may be impractical or difficult to move the image sensor and/or the light emitters into an operable proximity, and even where it is possible, the size of the object space in the direction perpendicular to the image sensor may still be too limited and/or the size of the object space in the directions parallel to the image sensor may be too limited. As has been shown above for a few examples, the size of the object space (e.g., in a direction perpendicular and/or parallel to the image sensor) may be limited and may be smaller than the volume in which the light emitters are located.

Embodiments of the present disclosure address this and other problems in the art.

For example, image sensors described herein can be associated with a lens system—positioned between the image sensor and the object space comprising the light emitters—so that the available object space is shifted away from the image sensor and/or increased in direction perpendicular to the image sensor. Preferably, the addition of a lens system creates an image space between the lens system and the image sensor where real images of the light emitters can be projected. Each real image of respective light emitters can then be identified and counted and/or positioned within the image space, as described above for light emitters. Because the properties of the lens system and image sensor (with associated structure) are known, the positions of the real images within the image space can be used, in some embodiments, to calculate the actual positions of the light emitters in the object space.

In other words, the limitations that have been formulated for the object space of embodiments without a lens system, discussed above, can now be applied to the image space (e.g., restriction of the object space in direction perpendicular to the image sensor can apply now to the image space) and the light emitters can be considered as being replaced by the real images of the light emitters. As a consequence, limitations for the object space can now be changed depending on the lens system. Thus, using the lens system allows for a more distant positioning of the object space with respect to the image sensor and also for a larger size of the object space especially in direction perpendicular to the image sensor. Preferably, the lens system is configured to create only real images of light emitters that are located in the object space and not virtual images. One reason for this is that real images of light emitters may be easier to identify in some embodiments because they represent close and localized apparent sources of light. Embodiments with a lens system may be constructed in the following manner: depending on, for example, the resolution requirements of the application or the amount of light collection, the image sensor with its pitch and the structure with its height may be selected and depending on requirements regarding the object space, a lens system may be selected with its appropriate optical parameters.

As such, embodiments of the present disclosure additionally enable the identification, counting, and/or positioning of light emitters within an object space that may otherwise have been difficult to identify, count, and/or position due to the relative distance between the image sensor and light emitters and/or between the light emitters within the object space.

Figure 11:
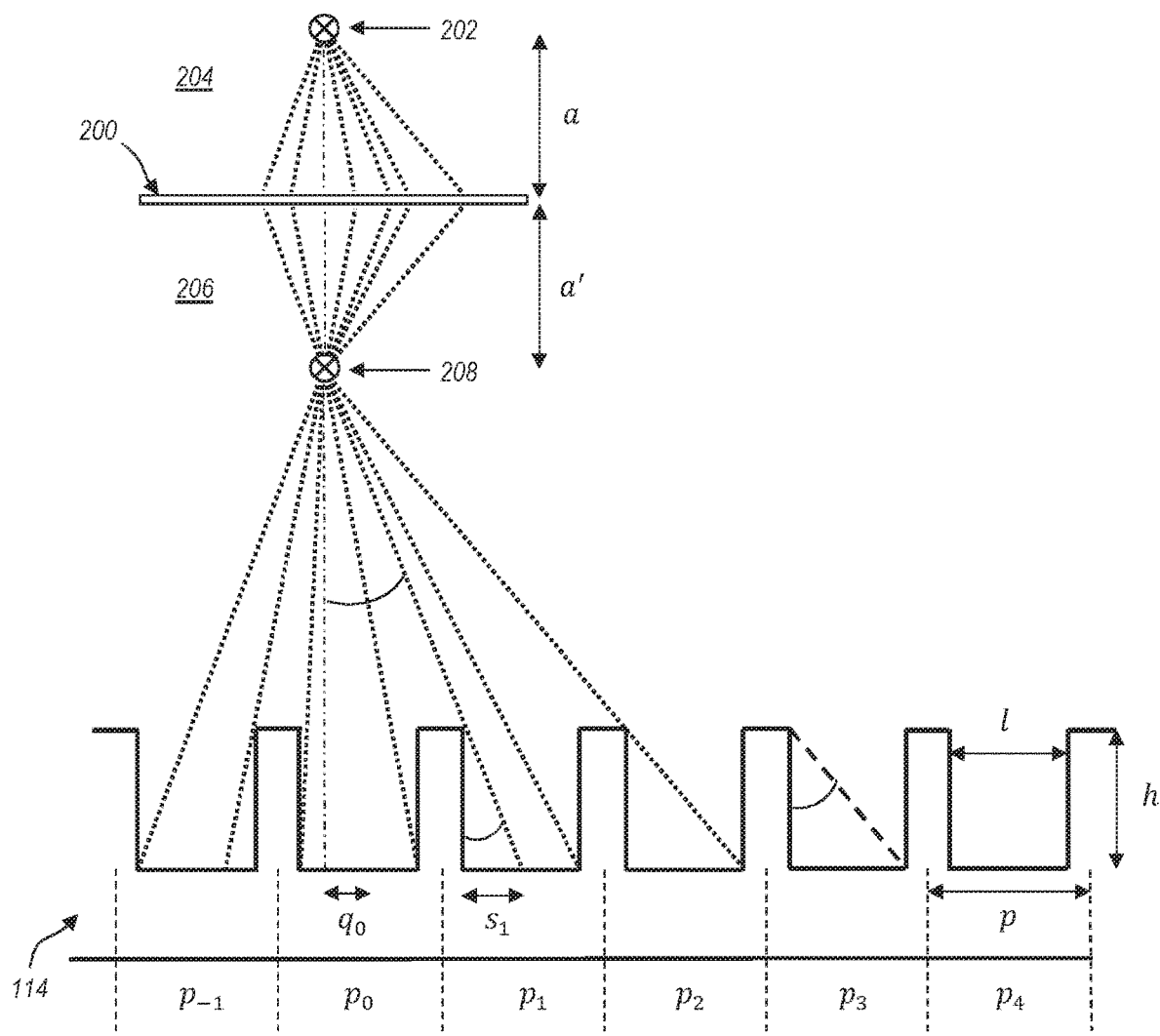
FIG. 11 illustrates a schematic of the image sensor of FIGS. 2-4 associated with an exemplary lens system.

Referring now to FIG. 11, illustrated is a schematic of the image sensor 114 of FIGS. 2-4 shown in association with an exemplary lens system 200. As shown, the lens system 200 is positioned between the image sensor 114 and the light emitter 202. The lens system 200 acts to functionally divide the viewable area of the image sensor 114 into an object space 204 on one side of the lens system 200 and an image space 206 on an opposing side of the lens system 200. The light emitter 202 is disposed within the object space 204 and projects light through the lens system 200. In turn, the lens system 200 projects a real image 208 of the light emitter 202 into the image space 206. The real image 208 can then be identified by the image sensor 114 (with associated structure), as provided above. The same or similar methods described above can additionally be used to calculate a position of the real image 208 relative to the image sensor 114.

In some embodiments, the lens system 200 has the effect of a converging lens (e.g., a biconvex lens), which, as shown in FIG. 11, produces a real image 208 of the light emitter at a distance, a', away from the lens system 200 in the direction of the image space 206. In some embodiments, the light emitter 202 and the real image 208 are equidistant from the lens. That is, the distance, a, of the light emitter 202 in the direction of the object space 204 is the same as the distance, a', of the real image 208 in the direction of the image space 206 (i.e., a=a'). In some embodiments, the lens system 200 comprises one or more lenses such that a≠a'.

When considering convergent lens systems described by a focal length f, the Gaussian lens equation for conjugate planes at a distance a and a' from the lens is:

$$\frac{1}{f} = \frac{1}{a} + \frac{1}{a'},$$

where a describes the distance of the object plane from the lens and a' describes the distance of the real image from the lens. In some embodiments, the Gaussian lens equation may be used to determine the parameters of the lens system 200 for a given image sensor 114.

In the context of FIG. 11 and where the light emitter 202 is positioned a distance, a, away from the lens system 200 such that the focal length of the associated lens, f, is less than a, the foregoing provides that the light emitter 202 within the object space 204 appears as a real image 208 in image space 206 a distance of a' away from the lens system 200. To the image sensor 114, the real image 208 appears to be a light emitter 202 that emits light. As such, the apparent light emitted by the real image 208 can be recorded by the image sensor 114 and used for an identification of the apparent light emitter (i.e., the real image 208 of the light emitter 202) and a determination of the position of the apparent light emitter.

In some embodiments, changes of the light emission characteristics of the apparent light emitter compared to the isotropic light emission of the actual light emitter can be taken into account when determining their relative positions. However, for counting applications, such compensation may not be incorporated, as long as the light emitters can be reliably identified as local maxima in the light intensity profiles measured by the pixels of the image sensor.

Generally, the lateral magnification of such lens systems is known to be M=a'/a and the angular magnification γ=a/a'. Accordingly, an increase of the object space over the image space in a direction perpendicular to the image sensor (i.e., a>a') causes an increase of the object space over the image space in direction parallel to the image sensor because the lateral magnification M is less than 1. Also, the angular magnification is increased, which may ensure that the light emission of the real image is wide enough so that every pixel of the image sensor that sees the real image (i.e., the real image is in the field of view of the pixel) also receives light from the real image. It should be noted, however, that the intensity of light emitted by the real image decreases as the angular magnification increases. It is also noteworthy that the lateral and angular magnifications depend on the relative distances of the light emitter and real image from the lens system and thus change when this ratio changes.

As a simple, non-limiting example, an image space may be restricted in the direction perpendicular to the lens (and thus, to the image sensor) to a distance z' away from the lens in the following way: f<z' and z'<2·f. According to the Gaussian lens equation, this allows recording of a light emitter in the distance z from the lens with 2·f<z and z<∞. This assumes that the image sensor can identify images of light emitters in the complete image space. For example, f may be selected within the range of 1 mm-2 mm for an image sensor having a pixel pitch of 1 μm and a wall height of 1 μm-2 μm.

In some embodiments, the object space may have a certain extension, for example 25 mm, in a direction perpendicular to the image sensor. For example, the light emitters in a sample vessel and the real images of the light emitters may be limited to:

$$\left(1+\frac{1}{10}\right)\cdot f < z' \text{ and } z' < \left(1+\frac{2}{10}\right)\cdot f.$$

This allows recording of light emitters in the distance z from the lens with approximately 6·f<z and z<11·f. Therefore, the object space is 50 times larger than the image space in the direction perpendicular to the image sensor. In embodiments where the image space has a perpendicular extension of 0.5 mm, which may be reasonable for a pixel pitch and wall height of around 1 μm, it follows that for f=5 mm, the object space has a perpendicular extension of 25 mm as required. Such an exemplary dimensioned object space is sufficient in certain embodiments to monitor a sample comprising light emitters disposed within a larger sample vessel, including standard sample vessels, as long as the liquid does not extend more than about 2.5 cm in vertical direction. As one exemplary embodiment using these foregoing values, the lens system can be mounted 3.5 cm above the liquid surface. When mounted in this way, the lateral magnification is in the range of around $\frac{1}{10}$–$\frac{1}{6}$ and the angular magnification is in the range of around 6-10.

In some embodiments, it may be preferable to have a smaller lateral magnification, and embodiments of the present disclosure enable the image space to be between two and sixty times smaller than the object space in a direction perpendicular to the image sensor. For example, it is possible to select a lens having a focal length of f=40 mm and to limit the distance z' of the real image to:

$$\left(1+\frac{15}{80}\right)\cdot f < z' \text{ and } z' < \left(1+\frac{16}{80}\right)\cdot f,$$

which is limiting approximately to 47.5 mm<z' and z'<48.0 mm. This allows recording of light emitters in the distance z from the lens with approximately 5·f<z and z<5.33·f, which limits z' approximately to 200 mm<z' and z'<213 mm. Therefore, the object space is around 26 times larger than the image space in direction perpendicular to the image sensor, the lateral magnification is around ¼, and the angular magnification is around 4.

Although shown as a single lens, it should be appreciated that the lens system 200 of FIG. 11, and other lens systems described herein, can include one or more lenses. Further, each lens and combination of lenses provided within disclosed lens systems can be selected in accordance with the type of lens system (e.g., convergent or telecentric lens system), focal lengths of the lenses, size of the object space, distance between the image sensor and light emitters, size and resolution of the image sensor, and/or the number, concentration, and/or intensity of light emitters within the object space.

For example, a lens system provided in association with the image sensor can include a first and a second convergent lens system that satisfies:

distance($L_1,L_2$)≥(2·$f_1$)+(2·$f_2$), where
$L_1$ represents the first convergent lens system,
$L_2$ represents the second convergent lens system,
$f_1$ represents the focal length of $L_1$, and
$f_2$ represents the focal length of $L_2$.

In such an exemplary embodiment, the real image viewed by the image sensor can be created by the second convergent lens system. In this example, objects that are farther than 2·$f_1$ away from the first convergent lens system have a first real image that is in the range between $f_1$ and 2·$f_1$ and also have a second real image generated by the second convergent lens system that is in the range between $f_2$ and 2·$f_2$ from the second convergent lens system. The total magnification can be calculated as the product of the two magnifications of each lens. It should be noted that in embodiments having two convergent lens systems without a telecentric relationship, further configurations may be used, but care should be taken to avoid the second image being a virtual image instead of the preferred real image.

Figure 12:
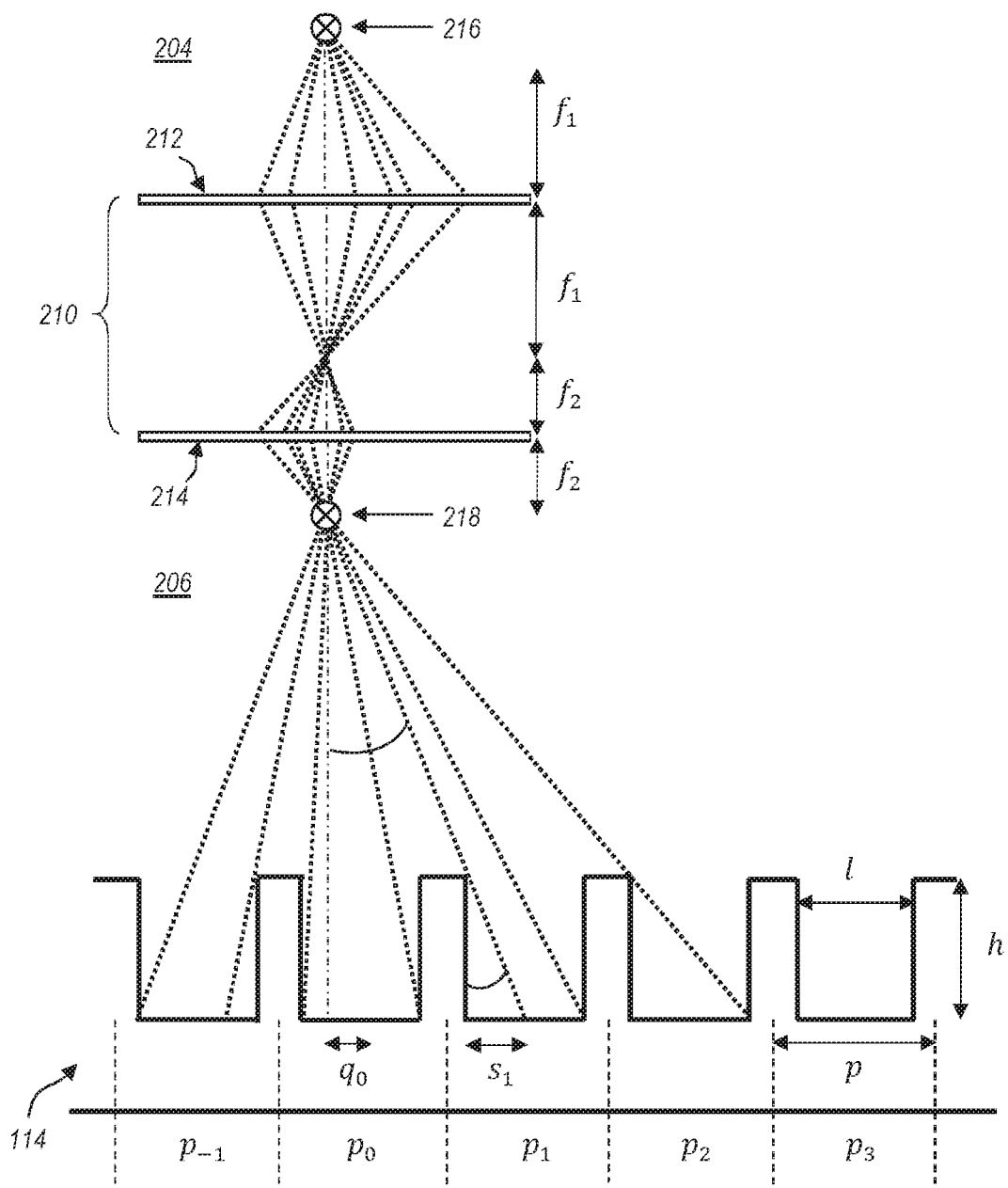
FIG. 12 illustrates a schematic of the image sensor of FIGS. 2-4 associated with another exemplary lens system.

In some embodiments, the lens system is a telecentric lens system. FIG. 12 illustrates a schematic of a telecentric lens system 210 that embodies the foregoing. As shown, the telecentric lens system 210 includes a first convergent lens system 212 and a second convergent lens system 214. The first convergent lens system 212 has focal length $f_1$ and the second convergent lens system has a focal length $f_2$ such that $f_1>f_2$. As shown, the first convergent lens system 212 is spaced apart from the second convergent lens system 214 at a distance equal to the sum of the focal lengths of each convergent lens system. The light emitter 216 is positioned within the object space 204, and the light emitted thereby is projected through the lens system 210 to create a real image 218 of the light emitter 216 (i.e., the second image generated by the lens system 210) within the image space 206. The real image 218 acts as an apparent light emitter, allowing the image sensor 114 to record light "emitted" from it. The same or similar methods described above can additionally be used to calculate a position of the real image 218 relative to the image sensor 114.

It should be appreciated that although the first and second convergent lens systems 212, 214 are illustrated as a single element in the schematic depicted in FIG. 12, the first and/or second convergent lens systems may have one lens or a plurality of lenses.

Further, in the telecentric lens system illustrated in FIG. 12, the lateral magnification is $M=(f_2/f_1)$, the angular magnification $\gamma=f_1/f_2$, and the axial magnification is $\alpha=M^2=(f_2/f_1)^2$. As can be seen from these equations, the magnification values are constant for given lens systems (i.e., they do not depend on the distance of the light emitter from the lens system) and the axial magnification, which can be beneficially adjusted, increases quadratically with the ratio of the focal lengths while the lateral magnification increases linearly.

As an example, a telecentric lens system may include a first lens system having $f_1=25$ mm, $f_2=5$ mm, so that $\alpha=1/25$, $M=1/5$, and $\gamma=5$. As such, an image space of 0.5 mm perpendicular size (which is appropriate for an image sensor having a pixel pitch of 1 μm and a wall height of 1 μm) will allow for an object space of 12.5 mm perpendicular size. More specifically, using the Gaussian lens equation for the first and the second lens, it can be calculated that an object space with a range of $f_1$ to $(1.5 \cdot f_1)$ (i.e., a perpendicular size of 12.5 mm) from the first lens will have a final image space in the range of $(0.9 \cdot f_2)$ to $f_2$ (i.e., a perpendicular size of 0.5 mm). More specifically, the distance $s'_1$ of an image of a light emitter at distance $s_1$ generated by the first lens is $$s'_1 = f_1 \Big/ \left(1 - \frac{f_1}{s_1}\right).$$

Distances $s_1$ and $s'_1$ are with respect to the first lens. The distance $s'_1$ of the image of the first lens with respect to the first lens can be identified with the distance $s_2$ of a virtual object from the second lens through the following equation: $s_2=-s'_1+f_1+f_2$. The virtual object at $s_2$ has then an image at the distance $s'_2$ from the second lens which is given by $$s'_2 = f_2 \Big/ \left(1 - \frac{f_2}{s_2}\right).$$

It can also be calculated that an object space with a range of $(1.5 \cdot f_1)$ to $(2 \cdot f_1)$ (i.e., again a perpendicular size of 12.5 mm) from the first lens will have a final image space in the range of $(0.8 \cdot f_2)$ to $(0.9 \cdot f_2)$ (i.e., again a perpendicular size of 0.5 mm). This confirms that the axial magnification values are independent of the distance of the light emitter from the lens system and have the expected value of $\alpha=1/25$. Therefore, in an example the object space may be located between 50 mm and 37.5 mm in front of the first lens and the image space may be located between 4 mm and 4.5 mm behind the second lens. It should be noted that the object space may not arbitrarily extend in this way because objects that are too far away from the first lens system can produce a virtual second image, which should be avoided.

In a further example, $f_1$ may be equal to $f_2$ so that the magnification values are all equal to 1. The telecentric lens system may then be used to shift the space that can be monitored by the image sensor away from the image sensor without increasing this space.

It should be appreciated that although specific reference was made to image sensor 114 of FIGS. 2-4 when discussing the concepts illustrated within FIGS. 11 and 12, other image sensors are compatible and can be used with the lens systems described herein to achieve the noted and implicit benefits associated therewith. For example, the lens systems described herein can be associated with the image sensor 186 of FIGS. 9 and 10 or with any other image sensor described herein.

Apparatuses, Systems and Methods for Identifying a Plurality of Light-Emitting Droplets As described above, the systems and methods disclosed herein offer significant advantages over prior art microscopy systems and methods. The disclosed systems enable the three-dimensional positioning of light-emitting objects within an object space without moving the sample or a system of lenses through a series of z-sequences, thereby reducing cost and mechanical/operational complexity of the imaging systems. Additionally, images can be obtained more quickly and with a reduced digital storage cost (e.g., because an associated computing system only stores data corresponding to a single image instead of data corresponding to stacks of images and the spatial relationships between each image of the stack).

With respect to fluorophore-based light emitters, the disclosed systems and methods beneficially reduce the amount of time fluorophores are exposed to excitation light without sacrificing the precision by which the positions of the light emitters are determined within the sample. For example, a single image can be captured and the position of one or more light emitters determined therefrom.

Additionally, or alternatively, the systems and methods disclosed herein enable the identification of multiple light emitters within the object space of the image sensor. The operable range and breadth of the object space can be increased through the addition of an intervening lens, as described, for example, in FIGS. 11 and 12. This can equate to a greater operating distance between the image sensor and the sample and/or an object space having a larger operable volume (e.g., increase the width, length, and/or depth of the object space).

Many of the foregoing and other benefits of the disclosed systems advantageously enable various practical applications of this technology. For example, there is an outstanding problem in the art of nucleic acid monitoring and visualization during various implementations of PCR, such as digital PCR (dPCR). The various implementations of dPCR can be used to directly quantify and clonally amplify nucleic acid templates, including single or double stranded DNA, cDNA or RNA, with greater precision than traditional PCR methods, as known in the art. Instead of acquiring a single data point in traditional PCR approaches, dPCR separates a sample into a large number of discrete small-volume reactions. Each of the small-volume reactions is typically associated with a reporter molecule (e.g., nucleic acid probes comprising a fluorescent dye and a quencher such as TaqMan® probes available from Thermo Fisher Scientific Inc., nucleic acid intercalating dyes such as ethidium bromide, nucleic acid groove binding dyes such as Hoechst dyes, nucleic acid stains such as SYBR® Green dyes available from Thermo Fisher Scientific Inc., and other fluorescent markers known in the art), and following thermal amplification cycles, the presence and concentration of amplicons within each small-volume reaction can be determined. From these data, and based on the notion that the sample has been distributed randomly (i.e., following a Poisson distribution) into each of the small-volume reactions, a precise measurement of the quantity of the target sequence can then be determined.

Droplet PCR or emulsion PCR is a subset of digital PCR. In droplet PCR methods, a water in oil emulsion is prepared with droplets that contain few or no single target nucleic acid molecules. Statistically, it may be expected that there is less than one target nucleic acid molecule in each droplet (e.g., an average of 0.5 or less target nucleic acid molecules per droplet). The droplets are then thermally cycled in a PCR process and after a sufficient number of cycles, the droplets that emit fluorescence are identified as droplets in which at least one target nucleic acid molecule was present before the PCR cycling. Measuring or calculating the total number of droplets allows a determination of the total number of target nucleic acid molecules that were present in the volume of aqueous sample used to prepare the droplets.

Thermal cycling of droplets in droplet PCR is typically performed within an emulsion located in a sample vessel. Due, at least in part, to the difficulty of standard optical systems to measure droplets in a large volume (e.g., because the depth of field is too small and many of the droplets are too blurry to be identified), the measurement of droplet fluorescence is usually spatially divorced from the thermal cycling. That is, prior art systems may force the user to sequentially measure the fluorescence of droplets. This typically requires moving the emulsion from the sample vessel to a different container of an optical system that is capable of sequentially identifying the droplets exhibiting fluorescence. This may require moving the emulsion from one apparatus (e.g., the thermal cycler) to another apparatus (e.g., a fluorescence detector) that can align the droplets in a row so that they can be sequentially investigated. Thus, although theoretically possible, current technologies are inefficient in monitoring the fluorescence values of droplets in a sample vessel undergoing active thermal cycling. There is a need for systems and methods that identify fluorescent droplets in a sample vessel that may also be used for thermal cycling and/or for systems and methods that identify fluorescent droplets within a sample reservoir and monitor the increase of fluorescence during thermal cycling, particularly while the sample vessel is associated with the thermal cycler.

Systems and methods of the present disclosure solve one or more of the foregoing and other problems in the art of microscopic imaging, particularly identifying and/or monitoring light-emitting droplets in droplet PCR or similar. For example, the disclosed apparatuses for identifying a plurality of light emitting droplets include detector systems comprising an image sensor and associated walled-structure. These detector systems can accurately and quickly count the number of droplets within the same sample vessel and can be combined with a thermal cycler for cycling the emulsion in the sample vessel to identify and monitor droplet fluorescence while the droplets are in the sample vessel and/or remain associated with a thermal cycler. In some embodiments, a lens system is positioned between the image sensor and the sample vessel to increase the operable distance, further enabling additional variations and embodiments.

Referring now to FIG. 13, illustrated is a general schematic of a thermal cycling and imaging system 220 for identifying a plurality of light emitting droplets. As shown, the system 220 includes a sample vessel 222, optionally associated with a thermal cycling unit 224. The sample vessel 222 is configured in size and shape to hold a plurality of droplets and to transmit changes in temperature (e.g., during thermal cycling). In an exemplary embodiment, the sample vessel 222 is a microfluidics chamber housing an emulsion of small-volume droplets or an individual well of a multi-well plate or substrate. As used herein, the term "small volume" when referring to droplet volume is intended to be on the nanoliter to picoliter scale. For example, a small-volume droplet can have a volume less than 100 nL, less than 10 nL, less than 1 nL, less than 100 pL, less than 10 pL, less than 1 pL, less than 100 fL, less than 10 fL, less than 1 fL, or a volume within a range selected from the foregoing volumes as endpoints (e.g., between 1 fL-1 pL, between 10 pL-100 nL, between 10 nL-10 pL, between 10 nL-100 pL, between 1 nL-100 pL, or between 1 nL-10 pL). In an example, the droplets may have a diameter between 0.5 μm and 10 μm which results in a volume between about 0.065 fL and 0.5236 pL. In a further example, the droplets may have a diameter between 2 μm and 5 μm.

The desired contents and droplet volume can be adjusted or selected, as known in the art. For example, the droplet contents and volume can be controlled when forming the emulsion. An emulsion can be created by flowing a discontinuous phase fluid into a continuous phase fluid of opposite polarity. In various exemplary embodiments, a continuous phase can be can include an oil (e.g., mineral oil, light mineral oil, silicon oil) or a hydrocarbon (e.g., hexane, heptane, octane, nonane, decane, etc.) and the like. The composition of the continuous and discontinuous phases can be selected at the discretion of the practitioner, though generally, the composition of the various phases can be selected to provide a suitable emulsion under thermal cycling conditions. As used herein, the term "suitable emulsion" and equivalents refers to an emulsion that does not substantially degrade or collapse or in which the hydrophilic compartments do not substantially coalesce under thermal cycling conditions. Therefore, in various exemplary embodiments, an emulsion can be suitable for carrying out reactions at varying temperatures (e.g., thermocycling), and other conditions (e.g., pH, ionic strength, hybridization conditions), and can contain various reaction components (e.g., sample nucleic acids, proteins, enzymes, catalysts, co-factors, intermediates, products, by-products, labels, probes, microparticles, etc.).

It should be appreciated that the aqueous droplets may have the same density as the oil of the emulsion so that they become more or less evenly distributed within the volume of the sample vessel. In some embodiments, the droplets may have a lower (or higher density) than the oil so that they have a higher concentration at a defined distance from the image sensor (e.g., where the image sensor has the highest effective resolution).

In one embodiment, the emulsion is generated such that each droplet contains PCR reagents. Additionally, each droplet can contain a fluorescent marker configured to indicate presence of the target nucleic acid. The fluorescent marker can include nucleic acid probes comprising a fluorescent dye and a quencher such as TaqMan® probes available from Thermo Fisher Scientific Inc., nucleic acid intercalating dyes such as ethidium bromide, nucleic acid groove binding dyes such as Hoechst dyes, nucleic acid stains such as SYBR® Green dyes available from Thermo Fisher Scientific Inc., and other fluorescent markers known in the art. In some embodiments, each droplet contains a droplet identifying fluorescent marker so that the apparatus can identify each droplet and differentiate the target-nucleic-acid-containing droplets from the non-target-nucleic-acid-containing droplets or identify the total number of droplets.

In some embodiments, each droplet contains a plurality of fluorescent markers. The emission wavelengths of each of the plurality of fluorescent markers can be different such that different multiplex PCR amplification products can be identified and/or monitored. In an exemplary embodiment, each of the plurality of droplets within an emulsion is formed such that each includes PCR reagents and buffers, polymerase, and one or more fluorescent markers. The concentration of sample may be varied by the practitioner. However, in some embodiments, each of the plurality of droplets within the emulsion is formed such that each includes (probabilistically) at least one copy of at least one target nucleic acid. In different embodiments, each of the plurality of droplets within the emulsion is formed such that each includes (probabilistically) less than one copy of at least one target nucleic acid.

In another exemplary embodiment, each of the plurality of droplets within an emulsion is formed such that each includes PCR reagents and buffers, polymerase, and at least two fluorescent markers. A first fluorescent marker can identify a first multiplex PCR amplification product, and a second fluorescent marker can identify a second multiplex PCR amplification product. Again, the concentration of sample may be varied by the practitioner. However, in some embodiments, each of the plurality of droplets within the emulsion is formed such that each includes (probabilistically) more than (or in some instances less than) one copy of at least one target site for multiplex PCR.

The sample vessel can include a multi-well plate or substrate, preferably a high-density multi-well plate or substrate. In one embodiment, the multi-well plate or substrate includes at least 96 wells configured to hold between 1 µL-200 µL of sample volume. The disclosed systems are additionally compatible with higher density multi-well plates, such as plates having 384 wells, 1536 wells, 3456 wells, 6144 wells, 9600 wells, or more. The volumes of each well can vary, as known in the art, but should preferably retain more than at least 100 nL of sample volume. It should be appreciated that other substrates can be used, such as microcards, microfluidics chambers, and the like—insofar as the droplets within the associated wells or sample vessels are within the object space of and viewable by the image sensor.

It should be appreciated that the selection of multi-well plate and/or substrate can affect the number and type of detector systems utilized within the thermal cycling and imaging system 220. For example, a single detector system can be integrated into the thermal cycling and imaging system 220 in situations where the entire sample vessel is within the operable object space of the associated image sensor. In some embodiments, additional detector systems can be permanently or removably associated with the thermal cycling and imaging system so that each sample vessel (or at least the droplets contained therein) fall within the operable object space of at least one image sensor.

With continued reference to FIG. 13, the thermal cycling and imaging system 220 can include an image sensor 114 and lens system 200, such as those described above. In some embodiments, the image sensor 114 and lens system 200 are configured in such a way that all droplets in the sample vessel 222 can be identified and counted. Stated another way, the image sensor 114 and lens system 200 are positioned relative to the sample vessel 222 such that the field of view of the image sensor 114 includes the whole cross section of the sample vessel 222 and such that the farthest and nearest possible distances from the image sensor 114 at which the image sensor 114 can identify light-emitting droplets includes the position of the sample liquid in the sample vessel 222. In short, all the droplets within the sample vessel 222 are located within the object space defined by the image sensor 114 and the additional lens system 200.

The thermal cycling unit 224 of system 220 is, in some embodiments, optional. When included, the thermal cycling unit 224 can be a standard thermocycler, as known in the art, or it may have components of a standard thermocycler and be disposed opposite the lens system 200 and image sensor 114 so as to not interfere with the line of sight between the image sensor 114 and the sample vessel 222. In this way, the sample vessel 222 or the droplets contained therein are not required to be moved for surveillance of fluorescence and the droplets within the sample vessel 222 may be monitored while simultaneously being thermally cycled. Among other benefits, such implementations enable the evaluation of how fluorescence within the droplets increases in real time, which can be used to more accurately compute the number of target nucleic acid molecules present in the droplets. In some embodiments, the lens system 200 and the image sensor 114 may be positioned above the sample vessel 222 that may be covered with a transparent foil or an oil to prevent evaporation during the cycling.

Referring now to FIG. 14, illustrated is an exemplary embodiment of a sample vessel 222 having a plurality of light emitting droplets 228 identified by an image sensor 114. As shown, the sample vessel 222 includes an emulsion of droplets during and/or following thermally cycling the emulsion. Fluorescent probes within each droplet act to differentiate subpopulations of the emulsion droplets by identifying those light-emitting droplets 228 having the target nucleic acid disposed and amplified therein. The remaining, non-target-nucleic-acid-containing droplets 226 can be clear, as shown, or in some embodiments, these droplets can include a different fluorescent marker so that the image sensor can positively identify each droplet within the emulsion and further differentiate the target nucleic acid containing droplets from the rest of the droplets.

Systems for identifying and/or monitoring light-emitting droplets can additionally include one or more light sources. As shown in FIG. 14, the system may include a light source 225 for illuminating the sample vessel 222. The light source 225 may be located next to the image sensor 114 and, when present, the additional lens system. The image sensor 114 may be located above the center of the sample vessel 222 (as shown) with the light source 225 positioned adjacent to the image sensor 114 so that it can illuminate the entire sample vessel 222, or at least the droplet containing portion of the sample vessel.

In one embodiment, two or more light sources may be located around the centrally positioned detector system. Additionally, or alternatively, a semi-transparent mirror or a dichroic mirror may be used to direct excitation light centrally from above the sample vessel into the sample and to provide emission light to the detector system. In such examples, the excitation light may be reflected by the mirror down into the sample and the emission light may pass through the mirror up to the to the image sensor 114 or it may be the other way around (i.e., excitation light may pass through the mirror and the emission light may be reflected by the mirror).

Accordingly, the disclosed systems can include one or more light sources 225 to illuminate the sample vessel 222. The light sources can be, for example, a white light or a light of a defined wavelength. In embodiments where the light-emitting droplets include a fluorophore (or a plurality of fluorophores), the light source can include one or more fluorophore excitation light sources. For example, a light engine comprising multiple LEDs each configured to emit an excitation wavelength (or range of wavelengths) for exciting fluorophores within the sample vessel can be positioned adjacent to the image sensor or around an optical axis of the lens system. Additionally, or alternatively, optical filters that filter the excitation and emission light, such as a multi-position dichroic filter wheel and/or a multi-position emission filter wheel can be associated with the image sensor, as appropriate.

As a general method of operation, a fluorophore excitation source can be automatically or manually directed to provide multiple bandwidths of light ranging from violet (e.g., 380 nm) to near infrared (e.g., at least 700 nm) and are designed to excite fluorophores, such as, for example, cyan fluorescent protein (CFP) and Far Red (i.e., near-IR) fluorophores. Example LED bandwidths with appropriate excitation filters (e.g., as selected via an excitation filter wheel) can include, but are not limited to, Violet (380-410 nm LED & 386/23 nm excitation filter), Blue (420-455 nm LED & 438/24 nm excitation filter), Cyan (460-490 nm LED & 485/20 nm excitation filter), Green (535-600 nm LED & 549/15 nm excitation filter), Green (535-600 nm LED & 560/25 nm excitation filter), Red (620-750 nm LED & 650/13 nm excitation filter), and Near-IR (700-IR nm LED & 740/13 nm excitation filter). The two Green/excitation filter combinations listed above can be provided optionally via, for example, a mechanical flipper, when desiring to improve the brightness of red and scarlet dyes. Of course, other LED bandwidths can also be used.

Referring now to FIG. 15, illustrated is an exemplary embodiment of a sample vessel 222 having a plurality of light-emitting droplets 228 where a real image 230 of the light-emitting droplets is identified by the associated image sensor 114 of the displayed detector system. Disposed between the image sensor 114 and the sample vessel 222 is a lens system 200. The lens system 200 makes the object space 204 accessible for identifying light emitters by creating an image space 206. In doing so, the operable distance of the image sensor 114 (i.e., the object space 204) is increased in a direction perpendicular to the surface of the image sensor 114. As shown in FIG. 15 (and as discussed in greater detail with respect to FIGS. 11 and 12), the lens system 200 positioned between the image sensor 114 and sample vessel 222 creates a real image 230 of the light-emitting droplets 228 such that the image sensor 114 can identify and count (and in some cases determine the three-dimensional location of) each of the light-emitting droplets 228, based on their corresponding real image projection 230.

Figure 16:
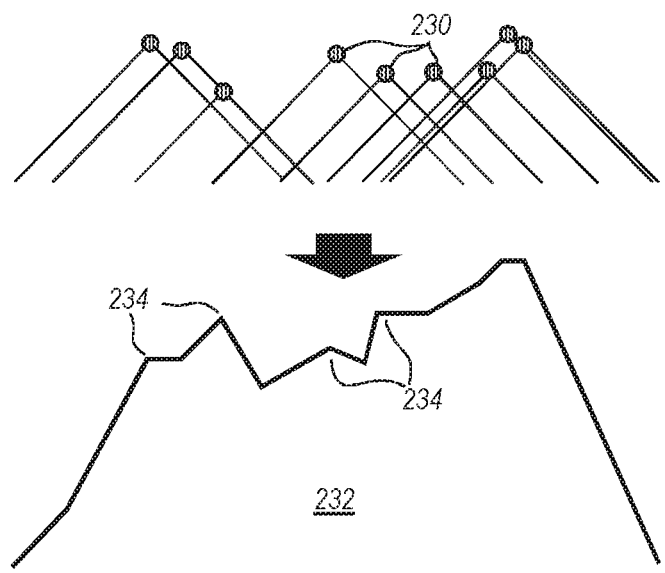
FIG. 16 is a diagram illustrating the plurality of light-emitting droplets from FIG. 14 or 15 and corresponding cones of light recorded by pixels of the associated image sensor and the resultant exemplary combined light intensity profile of the plurality of light-emitting droplets.

For example, the detector system (i.e., the lens system 200 and image sensor 114) of FIG. 15 can be associated with a sample vessel 222 to identify and count each light-emitting droplet 228 during or after thermal cycling and/or to monitor the fluorescence intensity of each light-emitting droplet 228 during thermal cycling. As mentioned above, this may be done by simple identification of local peaks in the light intensity values measured by the pixels. For ease of reference, the real-image projections 230 of each light-emitting droplet 228 of FIG. 15 have been reproduced in isolation within FIG. 16. As shown in FIG. 16, the real image 230 of the light-emitting droplet 228 is illustrated along with corresponding cones of light recorded by a row of pixels of the associated image sensor and the resultant exemplary combined light intensity profile 232.

The combined light intensity profile 232 is a combination of phenomena illustrated and discussed above with respect to FIGS. 5-8. For example, similar to FIGS. 7 and 8, the local maxima light intensities 234 can be first identified within the combined the light intensity profile 232 of FIG. 16. These local maxima 234 each correspond to individual light-emitting droplets and can be counted as such. Each of the light profiles associated with these light-emitting droplets can be subtracted from the combined light intensity profile 232 to allow for further identification of local maxima in the revised light intensity profile (not shown) and thereby continue counting the total number of light-emitting droplets. As described above, subtracting the light profiles of identified droplets from measured light intensity values can make a subsequent identification of further fluorescent droplets more sensitive.

After all of the light-emitting droplets have been identified, the number of target molecules originally present in the sample vessel 222 can be calculated. For embodiments in which there was statistically less than one target molecule in a droplet originally, the number of original target molecules may be calculated in an approximation to be equal to the number of light-emitting droplets. This approximation neglects that originally, there may have been two or three or more target molecules in a light-emitting droplet. This approximation is better when the number of target molecules is much smaller than the total number of droplets. This approximation can be improved using the Poisson distribution which gives the probability distribution for one, two, or three or more target molecules in a light-emitting droplet depending on the average probability of having a target molecule in a droplet. For embodiments in which there was statistically more than one target molecule in a droplet originally, the number of target molecules in the droplets may be obtained by measuring the fluorescence intensity of each droplet after each thermal cycle and, for example, determine from the number of cycles required to reach a certain intensity value the original amount of target molecules.

In an example, the total number of droplets may be computed by dividing the total volume of water that has been used to create all droplets in the sample emulsion by the average volume of the droplets. The total number of droplets may also be measured using the control fluorophore discussed above that provides a certain wavelength of fluorescence to all droplets. It should be appreciated that a control fluorophore may be provided in a diluted concentration such that all droplets can be registered and counted but droplets with amplified products of a certain concentration have a greater fluorescence than droplets without amplified products. This can allow differentiation between the two types of droplets. From the total number of droplets, the total volume of original sample can be calculated by multiplying the total number of droplets with the average volume of droplets. From the number of original target molecules and from the total volume of original sample, the original concentration of the target molecules can be obtained by dividing the number of original target molecules by the total volume of original sample.

Alternatively, the certain wavelength may be different from the wavelength of the fluorophore indicating the presence of the amplified product so that droplets with amplified products can be identified by their color. This may require using an image sensor with a color filter array with filters that have a transmission characteristic that coincides with the emission light of two different fluorophores, as described above. Using a color filter array with two different filters can beneficially allow for the identification of all droplets in addition to those droplets that contain target amplicons.

Furthermore, using different color filter arrays, it is possible to monitor multiplex PCR which uses different colors for different amplification products.

It should be appreciated that the resolution of the image sensor should be high enough to distinguish between different droplets. For example, for droplets having a diameter of 2-5 µm, a pixel pitch of around 1 µm may be used. Using a small sensor of, for example, 3 mm long by 3 mm wide, 9 million pixels are available for counting droplets. This exemplary image sensor would provide a pixel per droplet ratio of nearly 200 for a sample divided into about 50,000 droplets.

In one embodiment, the density of droplets may be lower than the density of the oil so that the droplets collect at the surface of the emulsion. In such an embodiment, the lens system may be a telecentric lens system in which all magnification values are equal to 1. The telecentric lens system can be used to create images of the droplets at a distance from the image sensor at which droplets can be counted with the highest accuracy. Assuming that the ratio of pixel per droplet is 200 (as above) and placing the images of the droplets at a distance from the image sensor at which each image is seen by around 200 pixels on average (e.g., in an area of 14×14 pixels), it then follows that on average, most pixels record light from at most one droplet and only one droplet. It is clear that for such an example, the individual droplets should be very easily be identifiable as local maxima in the measured light intensity distribution. Accordingly, in some embodiments, the number of droplets, the droplet density, and the resolution of the image sensor can be adjusted in combination with a lens system (e.g. a telecentric lens system) to more quickly and easily identify and count light-emitting droplets. This can be particularly advantageous for multiplex PCR applications where a single droplet may be emitting multiple wavelengths of light.

Figure 17:
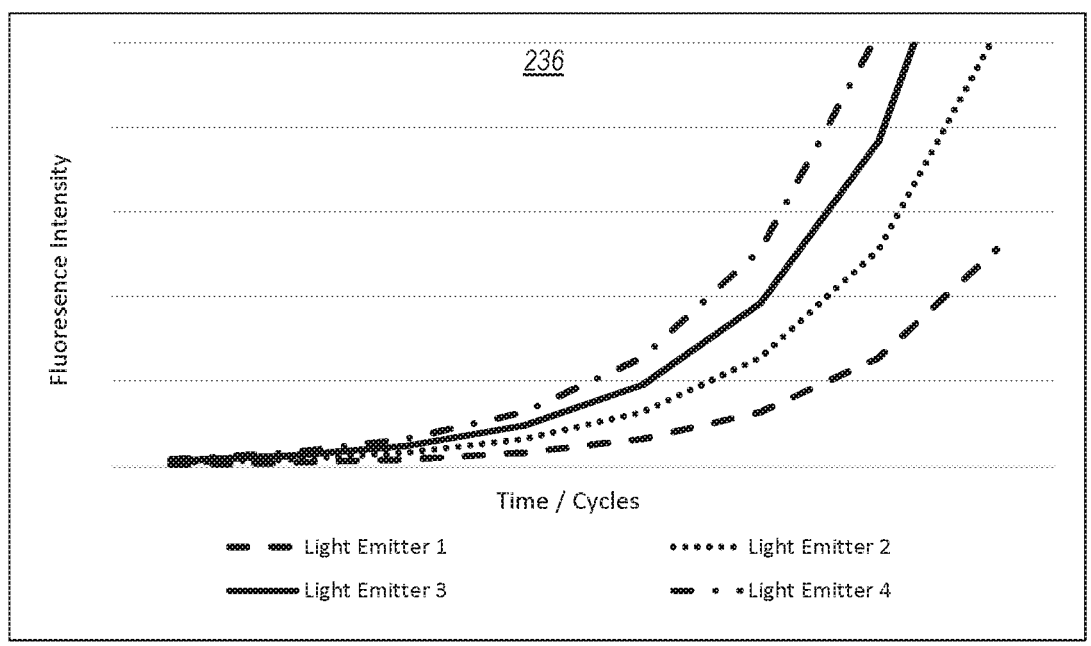
FIG. 17 illustrates an exemplary graph of fluorescence intensity exhibited by a plurality of light-emitting droplets during a thermal cycling process, as measured by an imaging system associated therewith.

Embodiments of the present disclosure advantageously enable the monitoring of fluorescence intensity while the droplets are being thermally cycled. This can provide a rich data source for calculating the relative or absolute amount of a target nucleic acid within a sample. As shown in FIG. 17, is an exemplary data set illustrating the measured fluorescence intensity of four different light emitters during a given thermal cycling protocol. As shown, each of the light emitters increase in fluorescence intensity at different rates, owing to the different number of target nucleic acid templates originally captured by the droplet.

In some embodiments, it can be advantageous to increase the probability that each droplet will have more than one copy of the target nucleic acid. As shown in FIG. 17, light emitter 1 started with a single copy of the target nucleic acid, light emitter 2 started with two copies of the target nucleic acid, light emitter 3 started with 3 copies of the target nucleic acid, and light emitter 4 started with 4 copies of the target nucleic acid. The relative fluorescence for each light-emitting droplet over time is represented in FIG. 17 as a function of the exponential growth of the template-derived amplicons. The data resolution provided by monitoring fluorescence intensity during thermal cycling is clearly superior to end-point fluorescence measurements, particularly in cases where the discernable difference between high fluorescence intensities becomes nominal even though there was an obvious quantitative difference in earlier cycles.

Similar to those systems described in FIGS. 11 and 12, it should be appreciated that although specific reference was made to image sensor 114 of FIGS. 2-4 when discussing the concepts illustrated within FIGS. 13-15, other image sensors are compatible with—and can be used with—the lens systems described herein to form a detector system for identifying a plurality of light emitting droplets and achieve the noted and implicit benefits associated therewith. For example, the lens systems described herein can be associated with the image sensor 186 of FIGS. 9 and 10 (or with any other image sensor described herein) and can form a detector system with the lens system 200 of FIG. 11 or the lens system 210 of FIG. 12.

It is to be understood that features described with regard to the various embodiments herein may be mixed and matched in any desired combination. In addition, the concepts disclosed or envisioned herein may be embodied in other specific forms. The described embodiments are to be considered in all respects only as illustrative and not restrictive. The scope is, therefore, indicated by the appended claims rather than by the foregoing description. All changes which come within the meaning and range of equivalency of the claims are to be embraced within their scope.

The invention claimed is:

1. An apparatus for identifying a plurality of light emitters, comprising:
  a detector system comprising:
    an image sensor comprising an array of pixels; and
    a structure associated with a surface of the image sensor, the structure extending a height away from the surface of the image sensor and defining a field of view for each pixel within the array of pixels,
  wherein a light emitter that is located in an object space is in the field of view of a plurality of pixels within the array of pixels and wherein the object space is limited in a direction perpendicular to the surface of the image sensor so that the light emitter is in the field of view of at least nine pixels and of less than 90% of the plurality of pixels within the array of pixels.

2. The apparatus of claim 1, further comprising a lens system positioned in front of the image sensor and defining an image space for the image sensor, wherein the lens system is configured to project a real image of the plurality of light emitters in the object space, the real image being located within the image space of the lens system, and the light emitter located in the object space being in the field of view of the plurality of pixels through the lens system.

3. The apparatus of claim 1, wherein the detector system is configured to monitor a presence of fluorescence within the plurality of light emitters and to monitor an intensity of fluorescence emitted by the plurality of light emitters, wherein the detector system monitors the fluorescence emitted by the plurality of light emitters by taking a plurality of images in a given time period so that a movement of each one of the light emitters is tracked and each one of the light emitters is identifiable over the given time period.

4. The apparatus of claim 1, wherein the light emitters are light emitting droplets and the apparatus further comprises a thermal cycler for cycling the plurality of light emitting droplets while the plurality of light emitting droplets is located in the object space.

5. The apparatus of claim 1, further comprising a light source configured to illuminate the object space.

6. The apparatus of claim 1, wherein the apparatus comprises a plurality of detector systems and a plurality of object spaces, wherein each object space is monitored by at least one detector system.

7. The apparatus of claim 6, wherein the plurality of object spaces has a pitch of 9 mm or a multiple of 9 mm and a total number of object spaces is 96 or a divisor of 96 or wherein the plurality of object spaces has a pitch of 4.5 mm and the total number of object spaces is 384.

8. The apparatus of claim 2, wherein the lens system comprises a convergent lens system.

9. The apparatus of claim 2, wherein the lens system comprises a telecentric lens system.

10. The apparatus of claim 9, wherein the telecentric lens system comprises two or more convergent lens systems, each adjacent pair of convergent lens systems being spaced apart a distance equal to a sum of the focal lengths of each lens in each convergent lens system of the adjacent pair of convergent lens systems.

11. The apparatus of claim 10, wherein each adjacent pair of convergent lens systems comprises:
a proximate convergent lens system; and
a distal convergent lens system,
wherein the proximate convergent lens system is positioned between the image sensor and the distal convergent lens system, and wherein the focal length of the proximate convergent lens system is less than or equal to the focal length of the distal convergent lens system, wherein an axial magnification of the adjacent pair of convergent lens systems increases the object space in a direction perpendicular to the image sensor.

12. The apparatus of claim 2, wherein the object space is extended between 0.5 mm and 30 mm in a direction perpendicular to the image sensor.

13. The apparatus of claim 2, wherein the image space is limited in a direction perpendicular to the surface of the image sensor to a range between 2 times the height of the structure and 1000 times the height of the structure and/or wherein the height of the structure is between 0.5 and 3 times the pixel pitch.

14. The apparatus of claim 1, wherein the structure is associated with a surface of the image sensor and comprises a plurality of walls positioned on pixel boundaries, forming a regular grid, wherein the plurality of walls is formed around each pixel.

15. A system for monitoring droplet polymerase chain reaction (PCR), comprising:
an apparatus as in claim 1, wherein the light emitters are light-emitting droplets;
an image processor configured to identify a number of light-emitting droplets within the plurality of droplets; and
a thermal cycler operably connected with the object space, wherein the object space comprises a plurality of droplets, a first subset of droplets of the plurality of droplets comprising PCR reagents, and a second subset of droplets of the plurality of droplets comprising a nucleic acid.

16. The system of claim 15, wherein the image processor is additionally configured to count the number of light-emitting droplets, wherein counting the number of light-emitting droplets comprises capturing a light intensity value at each photoactivated pixel of the image sensor and identifying local maxima of light intensity based on the light intensity values.

17. The system of claim 16, wherein counting the number of light-emitting droplets comprises:
capturing a light intensity value at each photoactivated pixel of the image sensor;
identifying a first light-emitting droplet, comprising identifying a local maximum of light intensity and a corresponding light profile associated with the local maximum;
subtracting the local maximum and the corresponding light profile from the captured light intensity values; and identifying subsequent light-emitting droplets for each remaining local maximum and corresponding light profile,
wherein identifying the light profile for the light emitting droplet comprises:
calculating virtual light intensity values for the first photoactivated pixel and the one or more photoactivated pixels, wherein a virtual light intensity value for a pixel represents the amount of light received by the pixel from a virtual light emitting droplet, the virtual light emitting droplet having the same first photoactivated pixel as the light emitting droplet;
comparing the virtual light intensity values with the light intensity values determined for light emitting droplet; and
identifying the light profile for the light emitting droplet with the light profile for the virtual light emitting droplet in the case that the virtual light intensity values are fitting to the light intensity values for the light emitting droplet within a tolerance level.

18. The system of claim 17, wherein the virtual light intensity value for the pixel is calculated based on a light receiving area of the pixel receiving light from the virtual light emitting droplet, wherein the virtual light intensity value for the pixel is calculated further based on a solid angle of the light receiving area of the pixel with respect to the virtual light emitting droplet.

19. A method for identifying light-emitting droplets, comprising:
thermal cycling a sample vessel comprising a plurality of droplets, wherein the plurality of droplets comprises droplet PCR reagents and a nucleic-acid-binding fluorophore, and wherein at least a subset of the plurality of droplets comprise nucleic acid; and
monitoring the sample vessel using a detector system, the detector system comprising an image sensor with an array of pixels, and a structure associated with a surface of the image sensor, the structure extending a height away from the surface of the image sensor and defining a field of view for each pixel within the array of pixels, wherein the sample vessel positions a sample within an object space of the detector system so that a light emitting droplet in the sample is in the field of view of a plurality of pixels within the array of pixels and wherein the object space is limited in a direction perpendicular to the surface of the image sensor so that the light emitting droplet is in the field of view of at least nine pixels and of less than 90% of the plurality of pixels within the array of pixels;
capturing a light intensity value at each photoactivated pixel of the image sensor receiving light; and
identifying a number of light-emitting droplets based on the light intensity values.

20. The method as in claim 19, wherein identifying a number of light-emitting droplets comprises:
(i) determining a local maximum of light intensity and a corresponding light profile associated with the local maximum;
(ii) subtracting the corresponding light profile associated with the local maximum from the captured light intensity values; and
(iii) repeating steps (i) and (ii) for each subsequent local maximum and corresponding light profile.

21. The method as in claim 19, wherein the detector system further comprises a lens system positioned in front of the image sensor and defining an image space for the image sensor, wherein the lens system is configured to project a real image of the plurality of light-emitting droplets in the object space, the real image being located within the image space of the lens system, and a light emitter located in the object space being in the field of view of the plurality of pixels through the lens system.

* * * * *